US007919255B2

(12) United States Patent
Prickett et al.

(10) Patent No.: US 7,919,255 B2
(45) Date of Patent: Apr. 5, 2011

(54) ASSESSMENT OF SKELETAL GROWTH USING MEASUREMENTS OF NT-CNP PEPTIDES

(75) Inventors: Timothy Charles Ramsey Prickett, Christchurch (NZ); Eric Arnold Espiner, Madison, WI (US); Arthur Mark Richards, Christchurch (NZ); Timothy Grant Yandle, Christchurch (NZ); Michael Gary Nicholls, Christchurch (NZ)

(73) Assignee: Otago Innovation Limited, Dunedin (NZ)

( * ) Notice: Subject to any disclaimer, the term of this patent is extended or adjusted under 35 U.S.C. 154(b) by 525 days.

(21) Appl. No.: 10/561,119

(22) PCT Filed: Jun. 17, 2004

(86) PCT No.: PCT/NZ2004/000125
§ 371 (c)(1),
(2), (4) Date: Apr. 13, 2007

(87) PCT Pub. No.: WO2004/111653
PCT Pub. Date: Dec. 23, 2004

(65) Prior Publication Data
US 2007/0292966 A1    Dec. 20, 2007

(30) Foreign Application Priority Data
Jun. 17, 2003 (NZ) ........................................ 526526

(51) Int. Cl.
G01N 33/53 (2006.01)
G01N 33/543 (2006.01)
G01N 33/563 (2006.01)
G01N 33/577 (2006.01)
G01N 33/68 (2006.01)
C07K 16/22 (2006.01)
C12N 5/20 (2006.01)

(52) U.S. Cl. ........ 435/7.1; 435/7.2; 435/7.92; 435/7.93; 435/7.94; 435/70.21; 436/512; 436/518; 436/547; 436/548; 530/388.2; 530/388.24; 530/388.25; 530/389.2; 530/389.3; 530/391.1

(58) Field of Classification Search .................... 435/7.1, 435/7.2, 7.8, 7.92, 7.93, 7.94, 70.21, 975; 436/518, 547, 548, 512; 530/388.2, 388.24, 530/388.25, 389.2, 389.3, 391.1
See application file for complete search history.

(56) References Cited

U.S. PATENT DOCUMENTS
2003/0219734 A1* 11/2003 Buechler .......................... 435/5

FOREIGN PATENT DOCUMENTS
WO    WO 01/14885 A2    3/2001

OTHER PUBLICATIONS

Prickett et al., 2001. Identification of amino-terminal pro-C-type natriuretic peptide in human plasma. Biochemical and Biophysical Research Communications 286: 513-517.*
Yasoda et al., 2000. C-type natriuretic peptide (CNP) as a novel skeletal growth factor: skeletal overgrowth of the transgenic mice that overexpress CNP specifically in cartilage. Journal of Bone and Mineral Research 15 (Suppl. 1): S243, Abstract SA050.*
Chusho et al., "Dwarfism and Early Death in Mice Lacking C-Type Natriuretic Peptide," Proc. Natl. Acad. Sci. USA, 98(7):4016-4021, Mar. 27, 2001.
Desai Meena, "Growth Disorders," Med. J. Armed Forces Ind., 59(4):278-282, 2003.
Hama et al., "A Monoclonal Antibody to C-Type Natriuretic Peptide—Preparation and Application to Radioimmunoassay and Neutralization Experiment," J. Endocrinology, 141:473-479, 1994, Odd pages only.
Harlow at al., "Immunizations," Antibodies: A Laboratory Manual, Cold Springs Harbor Laboratory, 53-137, 1988.
Huse et al., "Generation of a Large Combinatorial Library of the Immunoglobulin Repertoire in Phage Lambda," Science, 246:1275-1281, Dec. 8, 1989.
Kohler et al., "Continuous Cultures of Fused Cells Secreting Antibody of Predefined Specificity," Nature, 256:(5517): 495-497, Aug. 7, 1975.
Prickett et al., "Identification of Amino-Terminal Pro-C-Type Natriuretic Peptide in Human Plasma," Biochemical and Biophysical Research Communications, 286(3):513-517, 2001, Odd pages only.
Rasat et al., "IGF-1 and IGFBP-3 Screening for Disorders of Growth Hormone Secretion," NZ Med. J.,109: 156-159, May 10, 1996.
Stepan et al., "Expression of C-Type Natriuretic Peptide in Human Placenta and Myometrium in Normal Pregnancies and Pregnancies Complicated by Intrauterine Growth Retardation," Fetal Diagn. Ther., 17:37-41, 2002, Odd pages only.
Tanner et al., "Clinical Longitudinal Standards for Height and Height Velocity for North American Children," J. Pediatrics, 107(3):317-329, Sep. 1985, Odd only.
Prickett et al. Amino-Terminal proCNP: A Putative Marker of Cartilage Activity in Postnatal Growth. Pediatric Research vol. 58, No. 2, pp. 334-340, 2005.
Examination Report dated May 29, 2007 issued by the Intellectual Property Office of New Zealand in related NZ Application No. 553281.

(Continued)

Primary Examiner — Shafiqul Haq
Assistant Examiner — James L Grun
(74) Attorney, Agent, or Firm — Haynes and Boone, LLP

(57) ABSTRACT

A means of measuring and monitoring skeletal growth rate using a plasma analyte, amino-terminal C-type natriuretic peptide (NT-CNP). Plasma NT-CNP concentrations reflect the potential for further growth of the immature skeleton. Measurement of plasma NT-CNP in a subject, when related to the mean of an appropriate age and gender matched set of control subjects, provides an index of the severity of a growth disorder not otherwise available and facilitates diagnosis in children with undetected osteo-chondrodysplasias or other intrinsic disorders of the growth plate. The invention also provides a means of detecting and monitoring potentially harmful effects of drugs and other factors on skeletal growth long before they are evident using current methods in clinical practice.

34 Claims, 13 Drawing Sheets

OTHER PUBLICATIONS

Examination Report dated Jul. 14, 2008 issued by the European Patent Office in related EP Application No. 04 748 820.0, listing references D1-D10 cited by the European Examiner.

Stepan, H. et al., "Detection of C-type natriuretic peptide in fetal circulation," Journal of Perinatal Medicine, 28(2):118-121 (2000).

Vargas, S.J. et al., "Effects of Atrial Natriuretic Factor on Cyclic Nucleotides, Bone Resorption, Collagen and Deoxyribonucleic Acid Synthesis, and Prostaglandin E2 Production in Fetal Rat Bone Cultures," Endocrinology, Baltimore, MD, US, 125(5):2527-2531 (1989).

De Feo, M.L. et al, "Natriuretic Hormone Receptors and Actions on Bone Endothelial Cells," Endocrinology, Baltimore, MD, US, 133(4):1759-1766 (1993).

Mericq, V. et al., "Regulation of Fetal Rat Bone Growth by C-Type Natriuretic Peptide and cGMP," Pediatric Research, Williams and Wilkins, Baltimore, MD, US, 47(2):189-193 (2000).

Examination Report dated Nov. 17, 2008 issued by the Intellectual Property Office of New Zealand in related NZ Application No. 553281.

Examination Report dated Feb. 4, 2009 issued by the European Patent Office in related EP Application No. 04 748 820.0.

* cited by examiner

A

B

SEQUENCE LISTING

```
<160> NUMBER OF SEQ ID NOS: 6

<210> SEQ ID NO 1
<211> LENGTH: 103
<212> TYPE: PRT
<213> ORGANISM: Bos taurus

<400> SEQUENCE: 1

Lys Pro Gly Ala Pro Pro Lys Val Pro Arg Thr Pro Ser Gly Glu Glu
1               5                   10                  15

Val Ala Glu Pro Gln Ala Ala Gly Gly Gly Gln Lys Lys Gly Asp Lys
            20                  25                  30

Thr Pro Gly Gly Gly Gly Ala Asn Leu Lys Asp Asp Arg Ser Arg Leu
        35                  40                  45

Leu Arg Asp Leu Arg Val Asp Thr Lys Ser Arg Ala Ala Trp Thr Arg
    50                  55                  60

Leu Leu His Glu His Pro Asn Ala Arg Lys Tyr Lys Gly Gly Asn Lys
65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100

<210> SEQ ID NO 2
<211> LENGTH: 103
<212> TYPE: PRT
<213> ORGANISM: Ovis aires

<400> SEQUENCE: 2

Lys Pro Gly Ala Pro Pro Lys Val Pro Arg Thr Pro Pro Gly Glu Glu
1               5                   10                  15

Val Ala Glu Pro Gln Ala Ala Gly Gly Gly Gln Lys Lys Gly Asp Lys
            20                  25                  30

Thr Pro Gly Gly Gly Gly Ala Asn Leu Lys Asp Asp Arg Ser Arg Leu
        35                  40                  45

Leu Arg Asp Leu Arg Val Asp Thr Lys Ser Arg Ala Ala Trp Thr Arg
    50                  55                  60

Leu Leu His Glu His Pro Asn Ala Arg Lys Tyr Lys Gly Gly Asn Lys
65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100

<210> SEQ ID NO 3
<211> LENGTH: 103
<212> TYPE: PRT
<213> ORGANISM: Homo sapiens
```

<400> SEQUENCE: 3

```
Lys Pro Gly Ala Pro Pro Lys Val Pro Arg Thr Pro Ala Glu Glu
1               5                   10                  15

Leu Ala Glu Pro Gln Ala Ala Gly Gly Gln Lys Lys Gly Asp Lys
            20                  25                  30

Ala Pro Gly Gly Gly Gly Ala Asn Leu Lys Gly Asp Arg Ser Arg Leu
        35                  40                  45

Leu Arg Asp Leu Arg Val Asp Thr Lys Ser Arg Ala Ala Trp Ala Arg
    50                  55                  60

Leu Leu Gln Glu His Pro Asn Ala Arg Lys Tyr Lys Gly Ala Asn Lys
65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100
```

<210> SEQ ID NO 4
<211> LENGTH: 103
<212> TYPE: PRT
<213> ORGANISM: Mus musculus

<400> SEQUENCE: 4

```
Lys Pro Gly Thr Pro Pro Lys Val Pro Arg Thr Pro Gly Glu Glu
1               5                   10                  15

Leu Ala Asp Ser Gln Ala Ala Gly Gly Asn Gln Lys Lys Gly Asp Lys
            20                  25                  30

Thr Pro Gly Ser Gly Gly Ala Asn Leu Lys Gly Asp Arg Ser Arg Leu
        35                  40                  45

Leu Arg Asp Leu Arg Val Asp Thr Lys Ser Arg Ala Ala Trp Ala Arg
    50                  55                  60

Leu Leu His Glu His Pro Asn Ala Arg Lys Tyr Lys Gly Gly Asn Lys
65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100
```

<210> SEQ ID NO 5
<211> LENGTH: 103
<212> TYPE: PRT
<213> ORGANISM: Rattus norvegicus

<400> SEQUENCE: 5

```
Lys Pro Gly Thr Pro Pro Lys Val Pro Arg Thr Pro Gly Glu Glu
1               5                   10                  15

Leu Ala Glu Pro Gln Ala Ala Gly Gly Asn Gln Lys Lys Gly Asp Lys
            20                  25                  30

Thr Pro Gly Gly Gly Gly Ala Asn Leu Lys Gly Asp Arg Ser Arg Leu
        35                  40                  45

Leu Arg Asp Leu Arg Val Asp Thr Lys Ser Arg Ala Ala Trp Ala Arg
    50                  55                  60

Leu Leu His Glu His Pro Asn Ala Arg Lys Tyr Lys Gly Gly Asn Lys
65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100
```

```
<210> SEQ ID NO 6
<211> LENGTH: 103
<212> TYPE: PRT
<213> ORGANISM: Sus scroffa

<400> SEQUENCE: 6

Lys Pro Gly Ala Pro Pro Lys Val Pro Arg Thr Pro Pro Gly Glu Glu
1               5                   10                  15

Val Ala Glu Pro Gln Ala Ala Gly Gly Gln Lys Lys Gly Asp Lys
            20                  25                  30

Thr Pro Gly Gly Gly Ala Asn Leu Lys Gly Asp Arg Ser Arg Leu
        35                  40                  45

Leu Arg Asp Leu Arg Val Asp Thr Lys Ser Arg Ala Ala Trp Ala Arg
    50                  55                  60

Leu Leu His Glu His Pro Asn Ala Arg Lys Tyr Lys Gly Gly Asn Lys
65                  70                  75                  80

Lys Gly Leu Ser Lys Gly Cys Phe Gly Leu Lys Leu Asp Arg Ile Gly
            85                  90                  95

Ser Met Ser Gly Leu Gly Cys
            100
```

ASSESSMENT OF SKELETAL GROWTH USING MEASUREMENTS OF NT-CNP PEPTIDES

The present application is a U.S. national-stage patent application for international patent application PCT/NZ2004/000125, filed on Jun. 17, 2004, which claims priority to NZ 526526, filed on Jun. 17, 2003, the disclosures of each of which is incorporated herein by reference in its entirety.

FIELD OF THE INVENTION

This invention relates to amino-terminal CNP peptides and their use in diagnostic and prognostic testing for growth potential, and skeletal development and maturation in mammals including humans. More particularly, the invention relates to the use of these peptides in diagnosis and prognosis of growth, skeletal health, growth impairment, skeletal disorders and disease, and disorders of calcification in mammals, including humans.

BACKGROUND TO THE INVENTION

Growth of the long bones, initiated by paracrine factors, is engendered by recruiting chondrocytes from more primitive cells (mesenchymal cells of bone marrow) adjacent to the growth plate of the epiphysis. Linear growth in childhood results from endochondral ossification in the growth plate of long bones and vertebrae. For normal growth to occur there must be a co-ordinated sequence of steps involving (i) proliferation of chondrocytes within the growth plate, (ii) differentiation of chondrocytes to larger cells (hypertrophic phase) which lay down an extracellular matrix, (iii) apoptosis (programmed cell death) and mineralisation of matrix (ossification).

The proliferation phase is crucial to the growth process, and is regulated in health largely by paracrine and hormonal factors including growth hormone (GH), IGF-1, thyroxine and glucocorticoids. In humans, growth ceases, with disappearance of growth plates, after pubertal secretion of sex steroids which reduce chondrocyte proliferation and result in epiphyseal fusion.

Little is known of the paracrine factors affecting chondrocyte proliferation within the growth plate.

Of the many other factors present in growth plate tissues, and known to be important for normal growth, none has been shown to circulate in the blood at quantities sufficient for monitoring growth plate activity.

Indirect markers exist for assessing the growth potential in a subject. It is known, for example, in the art that a crude estimation of skeletal maturation (and hence potential for further growth) can be determined by a clinician examining an x-ray of the left wrist of a human. This provides an assessment of "bone age".

Unfortunately, the above process is highly subjective. Accuracy in measuring bone age is often dependent upon the skill and experience of the clinician.

Additionally, assessment of bone age using this technique cannot be used to detect short term changes in growth plate activity. This inability is particularly problematic in acute illness or during drug or other interventions, where influences on bone development could become an important indicator of progression of the disease or treatment. For example, over-medication of a patient with corticosteroids is known to adversely affect skeletal growth. An early indication of this would be useful to clinicians.

A need exists for an objective determination of skeletal growth in a subject. It would be desirable if such a determination involved the direct measurement of a circulating marker, changes in which correlated with changes to the rate of skeletal development in growing human infants and children. Such a determination would, for example, enable clinicians to objectively and more rapidly detect the overall rate of skeletal development or short-term changes in skeletal development in patients, and to amend treatment regimens to minimise any adverse effects on skeletal growth and development, if necessary.

It is an object of the present invention to go some way towards fulfilling this need and/or to at least provide the public with a useful choice.

SUMMARY OF THE INVENTION

The present inventors have surprisingly discovered that there is a correlation between skeletal growth and the concentrations of a circulating marker, NT-CNP (also known as NTproCNP or amino terminal proC-type natriuretic peptide), in humans and other mammals.

It has also been surprisingly discovered that the circulating concentration of NT-CNP is affected acutely in response to factors which are directly involved in increasing or decreasing skeletal growth. For example, circulating levels of NT-CNP decrease significantly in response to high doses of glucocorticoids which are known to inhibit skeletal growth in children. Such changes in levels of circulating NT-CNP can be detected within 24 hours of glucocorticoid treatment enabling a clinician to monitor the impact on skeletal growth of a drug dosage regimen and adjust the dosage if necessary to minimise any adverse effect on skeletal growth.

In a first aspect, the present invention provides a method for assessing skeletal growth of a subject, comprising measuring the level of NT-CNP in a biological sample from the subject, and comparing the level against the mean NT-CNP level from a control population, wherein a significant deviation in the measured level from the mean control level is indicative of abnormal skeletal growth.

Preferably the biological sample is plasma or whole blood.

Preferably the subject is a pre-adult, more preferably a pre-pubescent child, including infants and neonates.

In one embodiment the subject may be undergoing a treatment regimen which may impact on skeletal growth in said subject. Where a significant deviation from the mean control level is found, a clinician may amend the treatment regimen to minimise any adverse effect of the regimen on skeletal growth.

The measuring step may comprise detecting binding between NT-CNP and a binding agent that selectively binds NT-CNP. The binding agent is preferably an antibody or antibody fragment and is most preferably a monoclonal antibody or monoclonal antibody fragment.

Binding of NT-CNP is preferably measured using antibodies or antibody fragments that are immobilised to a solid phase.

This method may also be used to predict the skeletal growth potential of a subject whereby the NT-CNP level in a biological sample from said subject may be compared to the mean NT-CNP level of a control population that has attained maximum skeletal growth and what the maximum skeletal growth of the subject may be predicted from the NT-CNP level in the subject.

This method may also be used to predict the skeletal age of a subject whereby the NT-CNP level in a biological sample of said subject is compared to the mean NT-CNP level of a control population of known skeletal ages, and what the skeletal age of the subject predicted from the NT-CNP level in the subject.

In a second aspect, the present invention provides a method for diagnosing a skeletal disease or disorder in a subject comprising measuring the level of NT-CNP in a biological sample from said subject, and comparing the level against the mean NT-CNP level from a control population, wherein a significant deviation in the measured level from the mean control level is indicative of a skeletal disease or disorder.

Where a significant deviation from the mean control level is found, the method may comprise a further step of comparing the measured NT-CNP level with one or more mean NT-CNP levels from populations having known skeletal diseases or disorders to make a more accurate diagnosis of the specific disease or disorder.

The method may be useful in diagnosing a skeletal disease or disorder selected from the group comprising congenital disorders, delayed developmental disorders and advanced development syndromes.

The present invention further provides a method of monitoring skeletal growth in a subject comprising measuring the level of NT-CNP in a first biological sample from the subject and measuring the level of NT-CNP in a second biological sample, wherein the second biological sample is taken from the same subject as the first sample but at a later date, and comparing the levels of NT-CNP in said first and second samples, wherein a significant change in the level of NT-CNP in said second sample from the level of said first sample indicates a change in the rate of skeletal growth.

In one embodiment, the subject may be undergoing a treatment regimen which may impact on skeletal growth of said subject. Where a significant change in the level of NT-CNP in the second sample is found, a clinician may amend the treatment regimen to minimise any adverse effect on skeletal growth. Alternatively, an amendment in the treatment regimen may have been implemented after the NT-CNP level was measured in the first sample and the impact on skeletal growth assessed in the second sample. Further amendment of the treatment regimen may or may not be required depending on the NT-CNP level in the second sample as will be appreciated by a skilled reader.

In a further aspect the present invention provides a kit for measuring the level of NT-CNP in a biological sample comprising a binding agent that selectively binds to NT-CNP and which can be quantitatively meapured upon binding to NT-CNP.

Preferably the binding agent is selected from the group comprising an anti-NT-CNP antibody, an NT-CNP receptor, or functional fragments or combinations thereof.

The agent may be measured by chromatography, oxidation/reduction, fluorescence, luminescence, mass, molecular weight, radioactivity, or any combination thereof.

In another aspect, the invention provides a NT-CNP binding agent that selectively binds NT-CNP for use in assessing or monitoring skeletal growth in a subject.

The invention further provides a NT-CNP binding agent that selectively binds NT-CNP for use in predicting the skeletal growth potential of a subject, or for predicting the skeletal age in a subject.

The invention also provides a NT-CNP binding agent that selectively binds NT-CNP for use in diagnosing a skeletal disease or disorder in a subject.

The invention is also directed to the use of a NT-CNP binding agent in the manufacture of a medicament for assessing or monitoring skeletal growth in a subject; for predicting skeletal growth potential or skeletal age in a subject; or for diagnosing a skeletal disease or disorder in a subject.

BRIEF DESCRIPTION OF THE DRAWINGS

The invention will now be described with reference to the figures in the accompanying drawings in which:

FIG. 11A and FIG. 11B: Effect of 4 days of treatment with a glucocorticoid (dexamethasone, 0.25 mg/kg/day) in 12 week old lambs (filled circles, n=8) and in adult sheep (open circles, n=8) on (A) plasma NT-CNP and (B) change (?) in plasma alkaline phosphatase activity (ALP). Values are mean±SEM;

Figure 1:
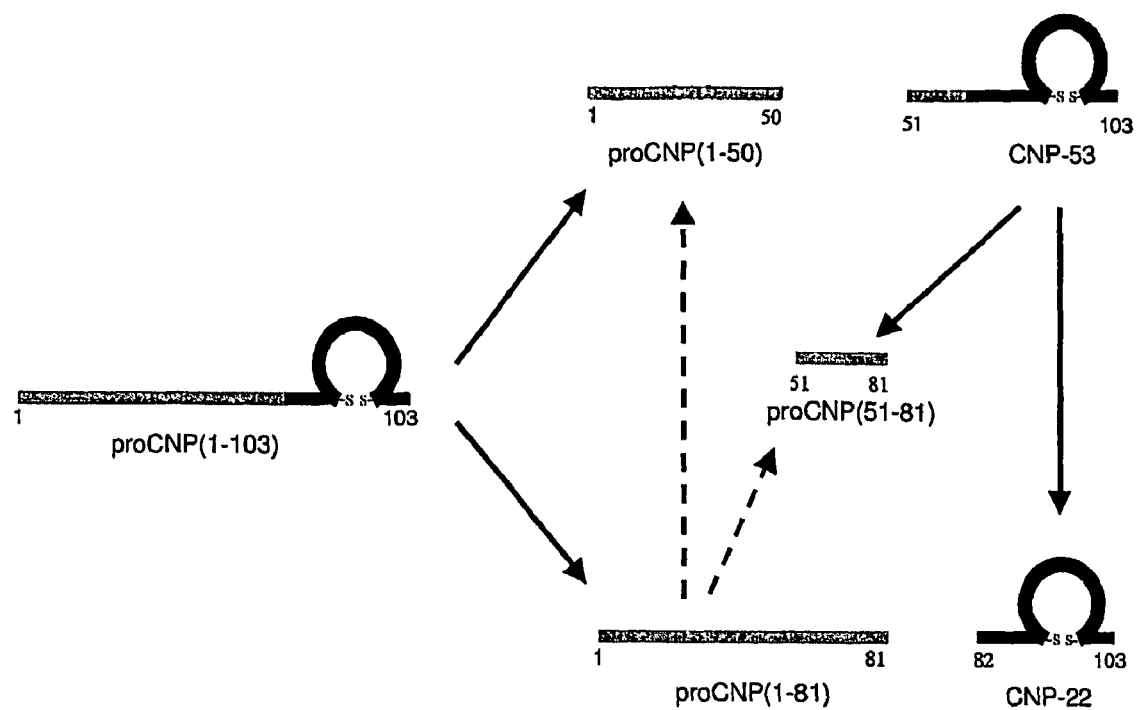
FIG. 1 is a scheme showing hypothetical processing of proCNP to CNP-22, CNP-53 and amino terminal CNP fragments.

FIG. 12A, FIG. 12B, FIG. 12C and FIG. 12D: Effect of a glucocorticoid (dexamethasone, 0.25 mg/kg/day) (filled circles, n=8) or saline control treatment (open circles, n=8), administered to 4 week old lambs for 15 days, on (FIG. 12A) plasma NT-CNP (FIG. 12B) plasma alkaline phosphatase activity (FIG. 12C) metacarpal length and (FIG. 12D) body weight. Values are mean±SEM; and FIG. 13: Shows a receiver operator curve (ROC) for different cut off values of plasma NT-CNP concentrations used to predict inhibition of growth velocity measured 15 days later. Inhibition of growth is defined as a concentration of growth velocity less than 5% of normal.

DEFINITIONS

In the present invention:
1) "Biological fluid" includes plasma, blood, or serum; urine; synovial fluid, cerebrospinal fluid, lymph, seminal fluid, amniotic fluid or any other body fluid.
2) "Endochondral calcification/ossification" refers to the process of chondrocyte formation, proliferation, maturation and ossification, whether in or outside the skeleton.
3) "Level" is intended herein to refer to the amount per weight or weight per weight. It is also intended to encompass "concentration" expressed as amount per volume or weight per volume.
4) "Growth plate activity" includes but is not limited to the rate of endochondral bone growth
5) "Skeletal disorders" Skeletal disorders include but are not limited to the following disorders affecting the immature skeleton (i.e. as found at birth, and/or occurring prior to adulthood).
   i) Congenital disorders:
      Osteochondrodysplasias and osteochondrodystrophy including:
         Achondroplasia, hypochondroplasia, achondrogenesis group (type I-IV), spondylodysplasia group (including spondylometaphyseal dysplasia), metatropic dwarfism, short rib dysplasia group (with or without polydactyly), Atelosteogenesis group; Stickler dysplasia group, epiphyseal dysplasia, metaphyseal dysplasia group; dysostosis multiplex group; chondrodysplasia punctata; chondrodysplasia (Blomstrand type); chondrodystrophy group; brachrachia; mesomelic dysplasias (including acromesomelic dysplasia); bent bone dysplasia group; osteodysplastic primordial dwarfism group; dysplasias with increased bone density; dysplasias with defective mineralizations; Schwartz-Jampel syndrome; dyssegmental dwarfism; Pelger-Huet anomaly; opsismod dysplasia; Robinow syndrome; metabolic disorders including Hurlers syndrome.
   ii) Disorders of skeletal growth and maturation including:
      (a) Delayed development—including prematurity, intrauterine growth retardation, syndrome associated with growth failure (Russell Silver syndrome, Seckel syndrome, Noonan syndrome, progeria Cockayne syndrome, Bloom syndrome, Prader Willi syndrome); placental insufficiency syndromes; maternal subnutrition and/or drug use; infant subnutrition and/or chronic disease; psychosocial deprivation; hypothyroidism; Cushing's syndrome; glucocorticoid treatments and related therapy; pseudohypoparathyroidism; rickets; pituitary growth hormone deficiency; growth hormone insensitivity; Shox mutation; Turner's syndrome; collagen disorders; rheumatoid disorders; constitutional delay of growth and maturation; hypogonadism; delayed puberty; coeliac disease; Crohn's disease; intestinal malabsorption; mitochondrial cytopathies; Malignancies and leukemic states; Down syndrome; chronic anaemias; chronic renal disorders; tumour of bone and/or cartilage.
      (b) "Advanced development" syndromes associated with tall stature, including cerebral gigantism, Beckwith-Wiedemann syndrome; gigantism (pituitary growth hormone hypersecretion), sexual precocity, hyperthyroidism, Marfan syndrome, XYY syndrome, homocystinuria, congenital adrenal hyperplasia; Klinefelter's syndrome, Proteus syndrome, constitutional tall stature, familial tall stature
   iii) External factors including:
      Glucocorticoid treatments and related therapy; chemotherapy and cytotoxic drug therapy; irradiation therapy; Vitamin A toxicity or other drug or environmental factors including lead toxins affecting skeletal health.
6) "Skeletal maturation" is the process of skeletal aging to full development when epiphyses ossify, i.e. adult stage.
7) "Pre-adult" subject is a subject in which growth plate activity is continuing or expected to continue. Such subjects are expected to have not attained epiphyseal fusion.
8) "Cartilage maturation" is the process of cartilage aging to full developmental i.e. adult stage.
9) "CNP" is C-type natriuretic peptide, and refers to the biologically active peptides derived from the prohormone (proCNP(1-103)) that is the product of the CNP gene. The known biologically active peptides include CNP-53 (proCNP(51-103) and CNP-22 (proCNP(82-103)).
10) "NT-CNP" is amino-terminal pro C-type natriuretic peptide. It encompasses any discriminatingly detectable sequence of consecutive amino acids selected from the amino acid sequence present in proCNP(1-81).
11) "Reference interval" is defined as a figure within a statistical band of a representative concentration, or alternatively a figure with an upper and lower concentration.
12) "Skeletal" includes bone and cartilage and ossification.
13) "Subject" includes a fetus, neonate, child, pre-adult mammals, including humans.
14) "Binding agent" is any molecule that binds NT-CNP peptides, including antibodies from any species whether polyclonal or monoclonal, antibody fragments such as Fab and Fab2, humanized antibodies or antibodies modified in other ways including substitution of amino acids, and/or fusion with other peptides or proteins. It also includes receptors or binding proteins from any species or modified forms of them.

DETAILED DESCRIPTION OF THE INVENTION

C-type natriuretic peptide (CNP) is a member of a family of structurally related peptides that play an important role in the control of various bodily functions.

CNP has been found in a variety of tissues with significant levels in various tissues, including bone and cartilage. Recent evidence in rodents suggests that CNP may also be an important regulator of skeletal (including bone and cartilage) growth by virtue of actions which stimulate proliferation and hypertrophy of chondrocytes. Despite finding CNP in bone and cartilage, any role for CNP in human skeletal growth has to date been speculative.

Unfortunately, there is virtually no detectable CNP present in circulation as it is effectively sequestered and/or metabolised by cells. Therefore, detection of CNP, if at all possible, is close to the detection limit of most current analytical methods. Potential applications of plasma or serum CNP assays to detect or monitor vessel and skeletal disease are limited.

The present inventors have now determined that a correlation exists between circulating NT-CNP, which has considerably higher concentrations than CNP in plasma, and skeletal growth.

It has been noted by Tanner and Davies (2) that there is a progressive fall in skeletal growth rate from birth to pre-puberty.

The inventors have for the first time linked this steady state decline with a corresponding decline in circulating NT-CNP concentrations. Thus the measurement of circulating NT-CNP lends itself as a marker of skeletal growth.

Other non-skeletal sources of NT-CNP include the vascular endothelium, heart tissue, circulating blood elements, stomach and reproductive tissues. The possible contributions of these non-skeletal sources to circulating NT-CNP in the growing period is likely to be small since (i) NT-CNP concentrations are not affected by heart disease (unless very severe), and are minimally affected by severe endothelial disease (as occurs in atherosclerosis which does not occur in children); (ii) NT-CNP is not affected by physical stress, e.g. surgical procedures; (iii) NT-CNP does not show diurnal fluctuation and is uninfluenced by meals. Therefore, in growing children, the skeleton is likely to be the main source of circulating levels of NT-CNP.

In adults, increased levels of osteoblastic activity (where alkaline phosphatase and osteocalcin are increased, for example Paget's disease of bone, osteomalacia and hyperparathyroidism) are associated with a small or no change in blood NT-CNP concentration.

Plasma concentrations of NT-CNP are affected by renal clearance and/or metabolism. Increased concentrations are observed in adults when renal function falls below 30% of normal. Interpretation of NT-CNP concentrations in children with moderate or severe renal failure may therefore provide results that are not representative of their skeletal development.

Ideally, before assessing skeletal growth or development using the methods of the present invention, a clinician would check renal function. This is particularly appropriate if there is reason to believe that a subject may have a renal disorders.

Where a subject is found to be suffering from a renal disease or disorder, the disease or disorder should ideally be addressed before conducting any of the methods of the invention. Fortunately, many renal disorders are treatable to obtain normal renal function. The NT-CNP concentrations are also expected to normalise within days of normalising the renal function in a subject so that the methods of the present invention are expected to provide more accurate results than before normalisation of such a renal disorder or disease.

TABLE 1

Plasma NT-CNP concentrations across surgery, meal and selected disease cohorts in adults.

| Subjects | Plasma NT-CNP concentrations (pmol/L, mean ± sem) |
|---|---|
| Across vascular surgery (n = 30) | |
| Day prior to surgery | 33 ± 3 |
| Day after surgery | 30 ± 3 |
| Across Day (n = 6, normal adults) | |
| 0900 hr | 24 ± 3 |
| 1200 hr | 23 ± 2 |
| 1300 hr (after meal) | 23 ± 2 |
| 1500 hr | 22 ± 2 |
| Atherosclerosis (n = 51)* | 33 ± 3 |
| Pagets Disease (n = 2)# | 22 ± 1 |
| Osteomalacia (n = 2)# | 28 ± 10 |
| Hyperparathyroidism (n = 1)# | 29 |

*Occlusive lower limb arterial disease.
Increased bone turnover with raised alkaline phosphatase activity.

The present invention therefore provides a method for assessing skeletal growth of a subject. The method comprises measuring the level of NT-CNP in a biological sample from the subject. The NT-CNP level is then compared against the mean NT-CNP level from a control population. A significant deviation of the measured level from the mean control level is indicative of abnormal skeletal growth.

The present invention may also be used to predict the final height which a pre-adult subject will attain. In such a method, the NT-CNP level in a biological sample of said subject is compared to the mean NT-CNP level of a control population that has attained maximum skeletal growth. The predicted maximum skeletal growth of the subject can be determined from the NT-CNP level by art-skilled workers.

The present invention is also useful as a method of diagnosis for a skeletal disease or disorder in a subject. The method comprises measuring the level of NT-CNP in a biological sample from said subject. The measured level is then compared against the mean NT-CNP level from a control population, wherein a significant deviation in the measured level from the mean control level is indication of a skeletal disease or disorder.

In particular, the method of the invention may be used to diagnose growth disorders and osteodystrophies, including chondrodystrophies and osteochondrodysplasia, that hitherto have been difficult to explain and difficult to categorise and diagnose.

The present invention also has application in the assessment of children presenting with a growth disorder eg. an abnormal concentration of NT-CNP outside the mean NT-CNP level of a control population is indicative of an intrinsic skeletal disorder, as well as indicative of the much more common disorder of simple constitutional growth disorder (for example, normal variant short stature or tall stature).

NT-CNP is measured in a whole blood or plasma sample by detecting binding between NT-CNP and a binding agent that selectively binds NT-CNP. Binding agents with specificity for NT-CNP and fragments are now described. Preferably the binding agent has low cross-reactivity with other mediators of growth and skeletal maturation. These binding agents may include antibodies or fragments thereof such as Fab, and F(ab)2, prepared using antigenic NT-CNP peptides or fragments thereof as immunising antigens. The polypeptides or fragments may also be coupled to a carrier as desired. Preferred binding agents are antibodies. These include monoclonal antibodies and polyclonal antibodies. These binding agents may be produced by any number of techniques available in the art. For reasons of specificity, monoclonal antibodies are currently preferred. It will be appreciated that humanised antibodies are not required for in vitro assays.

A preferred antigenic NT-CNP peptide comprises a partial consecutive sequence of proCNP(1-81) of a suitable size to enable antibodies and other immuno-molecules to be raised against the peptide. Preferably, the antigenic NT-CNP peptide comprises at least six consecutive amino acids from proCNP (1-81). This generally provides a sufficient epitope for specific amino acid detection. However, in some cases, it may be necessary to have at least eight amino acids to provide sufficient specificity for the peptide detection process.

In a currently more preferred embodiment, at least 15 consecutive amino acids from proCNP(1-81) is employed. For the best ability to raise antibodies, proCNP(1-81) can be employed itself. Other examples of peptides that could be used in raising antibodies include proCNP(1-50), proCNP(1-81), and proCNP(51-81) as set forth in FIG. 1 and FIG. 2. proCNP(1-103) can also be used in certain circumstances as antibodies raised may cross-react with proCNP(1-81) and proCNP(1-50) peptides. The peptides useful in the present invention are collectively referred to as NT-CNP in this application. The present invention also includes the use of functionally equivalent variants of the NT-CNP peptides.

Figure 2:
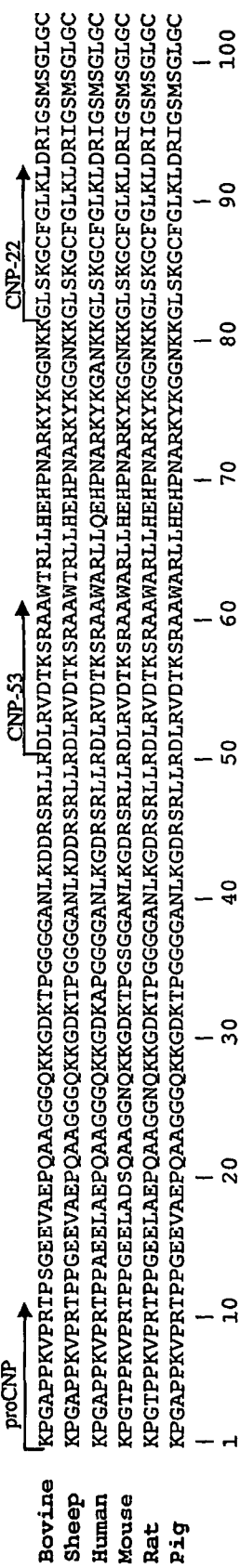
FIG. 2 shows the published amino acid sequences predicted for proCNP from gene/cDNA sequencing studies. The sequences for bovine, sheep, human, mouse, rat and pig proCNP sequences are aligned. Shaded positions are those that differ from the human sequence. These sequences are also included in the present application as SEQ ID NOS: 1 to 6 respectively.

The full length amino acid sequence of human proCNP(1-103) and other known mammalian proCNP sequences are shown in FIG. 2.

In a preferred embodiment, the antigenic NT-CNP peptide comprises NT-CNP(1-50), which the Applicants have demonstrated is a major NT-CNP peptide circulating in humans, or a functional fragment or metabolite thereof. proCNP(1-81) and proCNP(51-81) and their metabolites are also useful. These are predicted to arise and circulate as indicated in FIG. 1. It is likely that circulating NT-CNP levels or concentrations are reflective of CNP levels in bodily tissues and fluids.

Methods for raising antibodies and constructing immunoassays are well known in the art.

Monoclonal antibodies may be produced by known art methods. These include the immunological method described by Kohler et al (3) as well as the recombination DNA method described by Huse et al (4). The use of recombinant phage antibody systems to produce single chain variable antibody fragments, and subsequent mutation (such as site specific mutagenesis) or chain shifting to produce antibodies to NT-CNP peptides is also contemplated.

Conventional procedures for generating polyclonal antibodies are detailed in Harlow and Lane on pages 73 to 137 (5). Briefly, the protocol requires immunisation of a selected animal host such as a rabbit, goat, donkey, sheep, rat or mouse (usually a rabbit), with an isolated NT-CNP peptide on a number of spaced occasions, with one or more test bleeds preceding exsanguination and blood collection. Serum may be separated from clotted blood by centrifugation. Serum may be tested for the presence of polyclonal antibodies using ELISA or radioimmunoassay competitive assays or art equivalent methods.

Antibodies specific to proCNP(1-15), proCNP(36-50) and proCNP(67-81) can be raised after first conjugating these or similar peptides to a large protein such as bovine serum albumin or bovine thyroglobulin to make them immunogenic. Coupling can be effected by use of any protein crosslinking agent including for example the common agents glutaraldehyde, carbodiimide or N-(e-maleimido-caproyloxy) succinimide ester (MCS)—providing a cysteine residue is added to the peptide sequence prior to coupling. Injection of these conjugates into rabbits, sheep, mice or other species at monthly intervals followed by collection of blood samples two weeks later will enable production of polyclonal antibodies or monoclonal antibodies from the spleens of mice.

For example, the mouse host described above may be sacrificed and its spleen removed. The messenger RNA (mRNA) are then isolated and cDNA made from the mRNA using specific primers for the heavy and light chains of the variable region of the antibodies and the polymerase chain reaction (PCR) amplification. The DNA sequences for the heavy and light chains are joined with a linker sequence, to ensure the correct reading frame. Then the DNA construct will be inserted into a vector, for example, a plasmid or bacteriophage, or virus, for transformation into a host. A preferred vector is a bacteriophage.

Suitable hosts may be selected from prokaryotic, yeast, insect or mammalian cells. Preferably, a prokaryotic host, and most preferably *Escherichia coli* is used. The bacteriophage produces a viral coat and the antibody fragments are expressed on the coat, a phage display library. The phage display library can be screened for antibody fragments with the appropriate affinity for the specific antigens. The library can be screened many times and modifications can be made to the antibody construct through protein engineering techniques, such as site directed mutagenesis and chain shuffling all of which are within the capabilities of the art skilled worker.

Described herein is the use of a detection system involving the binding of NT-CNP to a binding agent and then detecting the amount of bound agent. A similar solution is to detect the amount of unbound binding agent in a sample to get an indication of unbound or bound NT-CNP. It is intended that such alternative methods fall within the scope of the present invention as functional alternatives to directly detecting the amount of bound binding agent. Art-skilled workers will appreciate that the concentration of NT-CNP in a sample can be readily calculated from the amount of NT-CNP in a sample when the sample volume is known.

The antibodies useful in the invention are particularly useful in immunoassays for determining the presence and/or amount of NT-CNP in a sample. Due to variable binding affinities of different antibodies, an art-skilled worker will appreciate that a standard binding curve of measured values versus amount of NT-CNP in a sample should be established for a particular antibody to enable the amount of NT-CNP in a sample to be determined. Such a curve is used to determine the true amount of NT-CNP in a sample.

Sample materials include cells, cell membranes and biological fluids but are not limited thereto. In terms of the present invention, usually a biological fluid is selected from whole blood, plasma, serum or urine. The sample is tested in vitro.

Immunoassays specific for NT-CNP peptides require the production of antibodies that specifically bind to NT-CNP peptides. One such preferred antibody recognizes amino acids within proCNP(1-15). These antibodies, while being specific for NT-CNP peptides have broad NT-CNP specificity. Antibodies useful in the invention preferably bind to one or more of the four peptides proCNP (1-50), proCNP(1-81), proCNP (51-81) and proCNP (1-103) (FIG. 1 and FIG. 2) or their metabolites. The antibodies can be used to construct immunoassays with broad specificity, as in competitive binding assays below, or used in conjunction with other antibodies described below in sandwich type assays to produce assays specific to each of the three peptides or to other NT-CNP peptides. Art-skilled workers will appreciate that non-competitive assays are also possible. The latter antibodies for sandwich immunoassays include those specific for amino acid sequences within proCNP(1-15), proCNP(36-50) and proCNP(67-81). These are preferred antibodies for use herein.

The methods may be performed using a kit as provided herein. A kit for measuring the level of NT-CNP in a biological sample is provided. The kit comprises a binding agent that selectively binds to NT-CNP and which can be quantitatively measured upon binding to NT-CNP. Preferred binding agents are as described above.

Indicators may also be used. Indicators may be employed in ELISA and RIA methods, which may be used herein.

Polyclonal and monoclonal antibodies can be used in competitive binding or sandwich type assays. The Applicants provide a competitive binding assay (radioimmunoassay format) in the example section of this application. In this method the liquid sample is contacted with the antibody and simultaneously or sequentially contacted with a labelled NT-CNP peptide or modified peptide containing the epitope recognised by the antibody.

The label can be a radioactive component such as $^{125}I$, $^{131}I$, $^{3}H$, $^{14}C$ or a nonradioactive component that can be measured by time resolved fluorescence, fluorescence, fluorescence polarisation, luminescence, chemiluminescence or colorimetric methods. These compounds include europium or other actinide elements, acrinidium esters, fluorescein, or radioactive material such as those above, that can be directly measured by radioactive counting, measuring luminescent or fluorescent light output, light absorbance etc. The label can also be any component that can be indirectly measured such as biotin, digoxin, or enzymes such as horseradish peroxidase, alkaline phosphatase. These labels can be indirectly measured in a multitude of ways. Horseradish peroxidase for example can be incubated with substrates such as o-Phenylenediamine Dihyhdrochloride (OPD) and peroxide to generate a coloured product whose absorbance can be measured, or with luminol and peroxide to give chemiluminescent light which can be measured in a luminometer. Biotin or digoxin can be reacted with binding agents that bind strongly to them; e.g. avidin will bind strongly to biotin. These binding agents can in turn be covalently bound or linked to measurable labels such as horseradish peroxidase or other directly or indirectly measured labels as above. These labels and those above may be attached to the peptide or protein: —during synthesis, by direct reaction with the label, or through the use of commonly available crosslinking agents such as MCS and carbodiimide, or by addition of chelating agents.

Following contact with the antibody, usually for 18 to 25 hours at 4° C., or 1 to 240 minutes at 30° C. to 40° C., the labelled peptide bound to the binding agent (antibody) is separated from the unbound labelled peptide. In solution phase assays, as in the example provided, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between NT-CNP in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays are more preferred for reasons of specificity, speed and greater measuring range. In this type of assay an excess of the primary antibody to NT-CNP is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to NT-CNP is also incubated with the sample either simultaneously or sequentially with the primary antibody. This second antibody is chosen to bind to a site on NT-CNP that is different from the binding site of the primary antibody. These two antibody reactions result in a sandwich with the NT-CNP from the sample sandwiched between the two antibodies. The second antibody is usually labelled with a readily measurable compound as detailed above for competitive binding assays. Alternatively a labelled third antibody which binds specifically to the second antibody may be contacted with the sample. After washing the unbound material the bound labelled antibody can be measured by methods outlined for competitive binding assays. After washing away the unbound labelled antibody, the bound label can be quantified as outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

In one embodiment, an antibody with specificity to ProCNP(1-15) is used.

Applications of NT-CNP in Skeletal Physiology and Skeletal Disorders

The invention may be applied in a number of different settings. Non-limiting examples of different applications relating to attaining final adult height are set out below:

1. Detection of poor growth potential in the newborn, in prematurity, intrauterine growth retardation and disorders of placental function. Estimation of growth plate activity and determination of the potential for growth (elongation) in newborn infants could be achieved as follows. A blood sample would be drawn from the umbilical vein or from another blood vessel in a neonate, the plasma separated and used to measure NT-CNP. The resultant plasma NT-CNP level would be compared with values from 20 or more neonates of the same gestational age and sex. Values outside the mean±2 sd would indicate reduced (<2 sd below the mean) or increased (>2 sd above the mean) growth in the succeeding month. Successive monitoring of plasma NT-CNP in neonates would provide a means of assessing benefits or effects of treatment strategies (such as improved nutrition, changed drug therapy) or other impacts suffered by the infant during the period of monitoring. Knowledge of growth plate activity at birth in the newborn infant at risk of growth failure would allow treatment strategies to be implemented before growth failure is clinically evident.
2. Detection of reduced or inappropriate levels of NT-CNP in children with impaired growth. This application estimates the current skeletal growth and, by inference, the growth plate activity and hence the likely increase in linear height over a defined subsequent period of 3-6 months in a child whose height is below the standard age and sex matched reference range. One could achieve this by drawing a blood sample from a vein of the child, separating the plasma from the red cells and measuring the plasma concentration of NT-CNP as described. The resultant level would then be compared with values determined from a representative sample of normal healthy children of the same age and sex (see for example Rasat R et al (6)). Values outside the mean of the representative sample±two standard deviations would indicate reduced (<2 sd or increased >2 sd) linear growth velocity in the following 3-6 months. In such children (with NT-CNP levels outside the reference range) more intensive diagnostic tests would be required, and closer monitoring of outcome planned. If the plasma NT-CNP level were to fall within the normal reference range, intensive testing and monitoring may not be necessary. In this application, the invention assists the clinician in distinguishing subjects requiring closer scrutiny from other subjects with growth disorders of lesser severity.
3. Detection of decreased or inappropriate levels of NT-CNP in congenital skeletal disorders and other osteodystrophies and chondrodysplasias.
4. Detection of increased or inappropriate levels of NT-CNP in infants with skeletal dysplasia including a disorder known as fibrodysplasia ossificans progressiva (FOP).
5. Discernment between infant skeletal dysplasia and progressive osseous heteroplasia (POH) which chiefly affects ossification within membranous bone rather than endochrondal bone. As stated, infant skeletal dysplasia is characterised by elevated or inappropriate NT-CNP levels whereas progressive osseous heteroplasia is not.
6. Detection of subjects with an intrinsic disorder affecting the CNP pathway within the growth plate: It can be anticipated that genetic disorders such as mutations in the CNP gene, its receptor, and post receptor genes or protein products will cause disorders of linear growth. In such subjects, who may present with a disorder of impaired or enhanced growth, a blood sample would be drawn and plasma NT-CNP measured on one or more successive occasions. Resultant levels inappropriately low when compared to subjects with similar age and growth velocity would indicate an intrinsic disorder of growth plate cartilage. Results inappropriately elevated when compared to subjects with similar growth velocity will indicate a disorder of CNP action whereby growth plate cartilage is resistant to the CNP formed within this tissue
7. Detection of increased or inappropriate levels of NT-CNP, compared to healthy normal children, will be found in some children with accelerated growth, familial tall stature and some other conditions associated with tall stature including Klinefelter's syndrome, Marfan's syndrome, XYY karyotype and premature puberty.
8. The development of NT-CNP in blood as an index of concurrent linear growth rate/and future potential for growth allows detection of subjects who have attained final (adult) height and whose growth plates have disappeared. "Skeletal age", also used to judge growth potential, represents the degree to which epiphyseal centres in long bones are ossified. In contrast, the level of NT-CNP in blood reflects the amount of actively proliferating cartilage remaining in the growth plates and therefore capable of extending long bones or vertebrae and allowing increases in linear height. Thus, the level of NT-CNP in blood provides an index of future growth potential not previously available. From knowledge of the normal reference range (currently being compiled in children and maturing adults), indexed to known parameters (gender, chronological age, absolute height, bone age and growth velocity)—all themselves referenced to the growth curves of normal children—see Tanner et al (2), the NT-CNP measurement provides the clinician with an objective assessment of the subject's future growth potential. Repeated measurements of NT-CNP in blood at specified intervals provides additional information on growth trends. This approach provides a means of monitoring and assessing efficacy of therapeutic interventions not otherwise available.

By way of example, the point of finally attained (adult, fully mature) height in a subject could be determined by drawing a blood sample from a vein, separating the plasma and measuring the plasma NT-CNP concentration as described. Resultant NT-CNP levels would be compared with a representative sample of NT-CNP levels from mature adults. NT-CNP levels that fall within the reference range encompassing 95% of mature adults will indicate cessation of linear growth and make the use of drugs or other strategies for height promotion ineffectual. Repeat measurements, for example 3 months apart, showing similar mature adult levels would be confirmatory in doubtful cases. Plasma levels above the mature normal adult reference range would indicate significant growth plate activity remaining and therefore further potential for increase in height. These methods of estimating growth activity in children approaching full skeletal maturity are superior to other current methods such as "bone age" which is determined from the subjects left wrist and takes no account of growth plates that actually contribute to increases in linear height.
9. Monitoring plasma NT-CNP in children during the course of treatment for acute lymphoblastic leukemia and other oncological disease. Changes in blood levels across chemo therapy or glucocorticoid treatment will alert clinicians to the skeletal impact of interventions and allow timely and appropriate changes in management. An example is the child with acute lymphatic leukaemia (ALL) receiving a treatment regimen, which includes glucocorticoids. These drugs are effective in reducing the malignant growth of lymphatic tissues but have the potential to inhibit linear growth in some children. It is difficult to predict the effect of any particular drug, or dose, on a child's growth which currently can only be determined by measuring heights 3-6 months or more after the glucocorticoid treatment has been commenced. The measurement of NT-CNP in the blood provides an early indication of the growth plate activity, and informs the clinician on the possible growth suppressing actions of the treatment. By way of an example, a blood sample will be drawn for measurement of NT-CNP from a child with ALL just prior to the start of a course of high dose prednisone or other glucocorticoid treatment. A further sample will be drawn at an interval of 2-7 days after the start of the glucocorticoid treatment. By comparing the concentration of NT-CNP in plasma taken before and during glucocorticoid treatment it will be possible to determine any significant inhibitory effects of the treatment on growth plate activity. A significant fall from the starting level would be an indication of future growth impairment. No significant difference from the starting level would indicate the treatment is unlikely to be harmful to growth plate activity. Further uses include repeated monitoring of the plasma NT-CNP concentration during the course of the glucocorticoid treatment. In children aged 3-10 yrs (which includes more than 80% of all ALL subjects), absolute levels of plasma NT-CNP (drawn during the glucocorticoid treatment) below the lower limit of an age and sex matched reference range (6) would indicate growth impairment. The invention enables the clinician to change the treatment, or the dose or the duration before impaired growth is apparent, using a technique not otherwise available. Monitoring the effects of these changes by repeated measurements of plasma NT-CNP provides a means of determining a treatment regimen which regulates and controls ALL but which avoids growth impairment.

Other examples, using a closely similar monitoring strategy, are applicable to children receiving inhaled or systemic glucocorticoids for asthma or other chronic allergic states, and to any other child receiving any other agent or drug injurious to growth. Similarly such a monitoring strategy can be used to determine the improving state of growth plate activity on withdrawal of growth suppressing agents, and to assess the value of agents, nutrients or drugs promoting growth.

10. Similarly, monitoring of children with such common disorders as asthma and other allergic states requiring glucocorticoids will allow detection of children at risk for impaired growth and bone structure.

Other applications of the assay will include adult and childhood subjects with abnormal skeletal formation including:

1. Detecting abnormal NT-CNP levels in biological fluid (including synovial fluid from joint aspiration) in subjects with loss of cartilage, as in osteoarthritis. "Abnormal" denotes a level outside the normal reference range for the subject's age and gender given regard to clinical status. Since an early step in the development of osteoarthritis is cartilage proliferation, sequential changes in NT-CNP provide information important in diagnosis and treatment.
2. Detecting abnormal NT-CNP levels in biological fluid (including synovial fluid from joint aspiration) in subjects with inflammatory skeletal conditions, including rheumatoid arthritis.
3. Detecting pathological states in which endochondral calcification occurs in soft tissues outside the skeleton.
4. Primary neoplastic skeletal states including chondromata, chondrosarcoma, osteogenic sarcoma and related disorders.
5. Detecting osteoblastic deposits in the skeleton of patients with malignancy including breast cancer and prostatic cancer.

The finding of an abnormal level of NT-CNP, and by implication a disorder affecting CNP synthesis or action in bone, is important inter alia because it focuses diagnostic attention on cartilage growth. Further, monitoring the level of NT-CNP will detect harmful or beneficial interventions rapidly, and allow treatment strategies to be formulated accordingly.

Statistical analysis of reference range results obtained using the methods described herein is possible using conventional statistical techniques in the art. Preferably, the statistical grouping should include 95% of the sample, more preferably 99% of the sample.

The invention will be described below with reference to the Examples, which are intended to illustrate the invention but are not intended to limit the scope of the invention.

EXAMPLES

Peptides: Human NT-CNP(1-15), human NT-CNP(1-15)-Tyr$^{16}$ and human NT-CNP(1-19) were synthesised by Mimotopes, Australia. Purity by mass spectrometry was 74%, 80% and 95% respectively.

Antiserum production: Human NT-CNP(1-15) (5 mg) was conjugated to 4.2 mg of bovine serum albumin (BSA, fraction V, GibcoBRL, Life Technologies) using 62.2 mg of 1-ethyl-3(3-dimethyaminopropyl) carbodiimide at pH 7 for 18 hours and dialysed against phosphate buffered saline. Rabbits were given a primary subcutaneous injection of the antigen after emulsification with an equal volume of complete Freunds adjuvant (Sigma Chemical Co., St Lois. Mo., USA). Subsequent injections using incomplete Freunds reagent were given at monthly intervals. Rabbits were bled two weeks after each injection and tested for binding of radioactive tracer and its displacement by NT-CNP (1-15) standards.

RIA for N-terminal CNP: NT-CNP(1-15)-Tyr$^{16}$ (5 µg) was iodinated using 0.5 mCi Na$^{125}$I in the presence of 10 µg chloramine-T in 5 µl 0.5M phosphate buffer, pH 7.5 for 30 seconds, followed by the addition of 50 µg cysteine, 25 µg BSA and 20 µg KI in 100 µl buffer. The resulting mixture was loaded onto a 10 m RP300 Brownlee column and eluted with a gradient from 0-60% acetonitrile in 49 mM KH$_2$PO$_4$ pH 2.9 over 30 min at 1 ml/min, collecting 0.5 ml fractions. The fraction containing the major peak of radioactive NT-CNP(1-15)-[$^{125}$I]Tyr$^{16}$ was used in the RIA. Peptide standards were made from synthetic human NT-CNP(1-19) taking into account the purity data supplied. All standards, sample extracts, antisera and tracer solutions were made up in RIA assay buffer consisting of 0.1% bovine serum albumin, 0.01% sodium azide, 0.1% triton X100, and 0.05% sodium chloride in 0.1M phosphate buffer pH 7.4. 200 µl of sample extract or 7-38,000 pM NT-CNP(1-19) standard (all in duplicate) were pre-incubated with 100 µl antiserum solution at a dilution of 1:6000 for 22 h at 4° C. prior to the addition of 100 µl tracer solution (NT-CNP(1-15)-[$^{125}$I]Tyr$^{16}$) containing 2000 cpm for a further 24 h at 4° C. Bound and free NT-CNP(1-15)-[$^{125}$I]Tyr$^{16}$ were separated by a solid phase second antibody method (Sac-cell, Donkey-Anti Rabbit, IDS Ltd, England).

RIA for CNP: Peptide standards were made from synthetic human CNP (Peninsula Laboratories, Inc. Belmont, Calif., USA). All standards, sample extracts, antisera and tracer solutions were made up in assay buffer consisting of 0.1% bovine serum albumin, 0.01% sodium azide, 0.1% triton X100, and 0.05% sodium chloride in 0.1M phosphate buffer pH 7.4. 100 μl of sample extract or 3-200 pM CNP standard (all in duplicate) were pre-incubated with 100 μl rabbit anti-C-Type Natriuretic Peptide-22 serum (Peninsula Laboratories, Inc. Belmont, Calif., USA) for 22 h prior to the addition of 8000 cpm [$^{125}$I] labelled [Tyr$^0$]-CNP (Peninsula Laboratories, Inc. Belmont, Calif., USA) and incubated for a further 24 h at 4° C. Bound and free [$^{125}$I] labelled [Tyr$^0$]-CNP were separated by a solid phase second antibody method (Sac-cell, Donkey-Anti Rabbit, IDS Ltd, England).

Extraction of peptides from plasma: Blood was collected into tubes containing EDTA, centrifuged and the plasma stored at −80° C. Plasma or urine samples (4-5 ml) were extracted using Sep-Pak C18 cartridges (Waters Corporation, Milford, Mass., USA) prewashed with 5 mL methanol and 5 mL 0.1% trifluroacetic acid. Plasma or urine was run slowly through the column, which was then washed with 5 mL 0.1% trifluroacetic acid. NT-CNP was then eluted with 80% isopropanol in 0.1% trifluroacetic acid and dried under an air stream at 37° C. after addition of 10 uL of 1% triton X100. Extracts were re-suspended in either 0.1% TFA or 20% CH3CN in 0.1% TFA or RIA assay buffer prior to size exclusion or reverse phase HPLC or radioimmunoassay respectively.

Results

Figure 4:
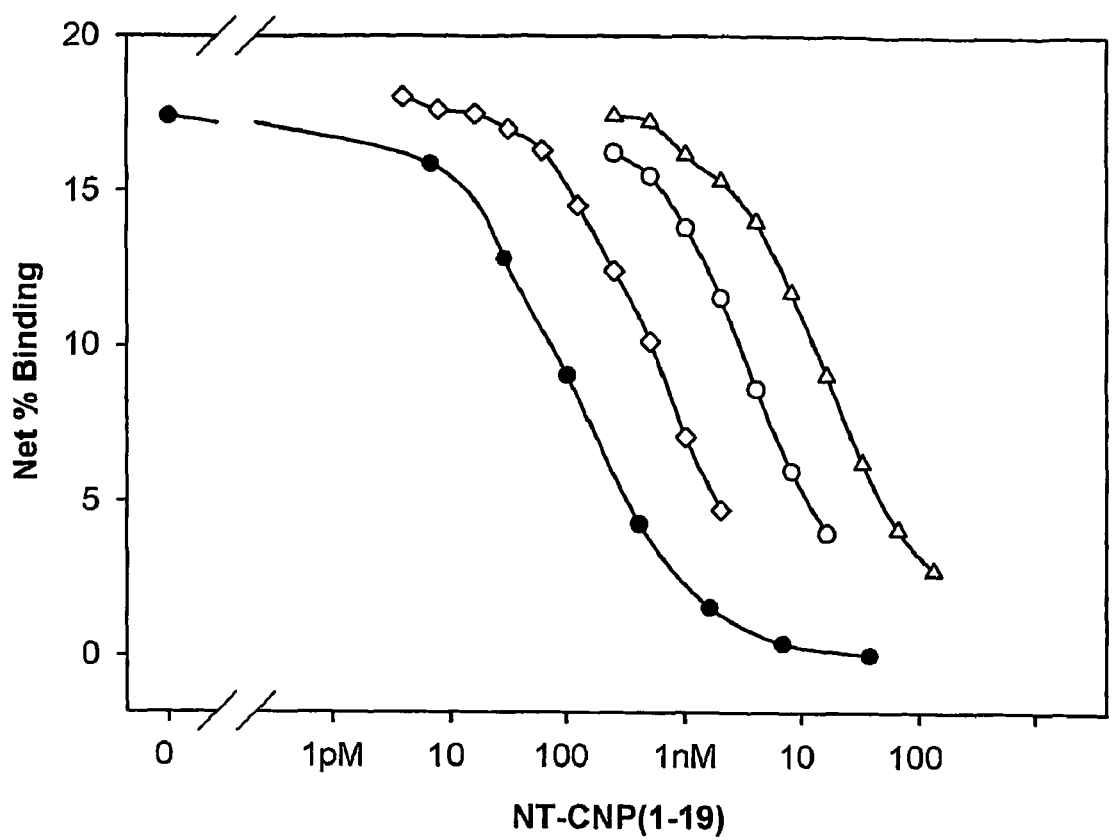
FIG. 4 is a graph showing the results of a NT-CNP radioimmunoassay. Serial dilutions of normal human plasma (open diamonds), pooled plasma extracts from children (aged 5-18 years) (open circles), pooled plasma extracts from patients with heart failure (open triangles) demonstrating parallel displacement of $^{125}$I labelled NT-CNP(1-15)Tyr$^{16}$ when compared to NT-CNP(1-19) standards (filled circles)
Figure 5:
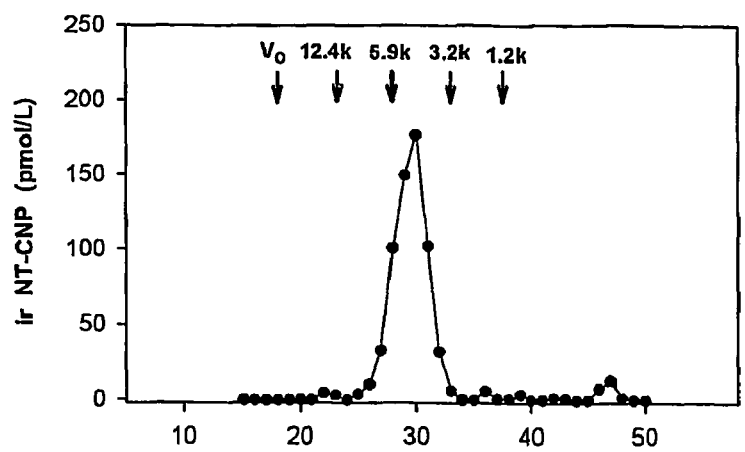
FIG. 5A, FIG. 5B, and FIG. 5C are graphs showing the results from size exclusion HPLC of immunoreactive NT-CNP (filled circles) and CNP-22 (open circles) in extracts of (FIG. 5A) EDTA plasma from normal adult human subjects, (FIG. 5B) pooled EDTA plasma obtained from children, and (FIG. 5C) EDTA plasma from sheep. Column void volume and the elution position of molecular weight markers are shown by arrows.
Figure 5:
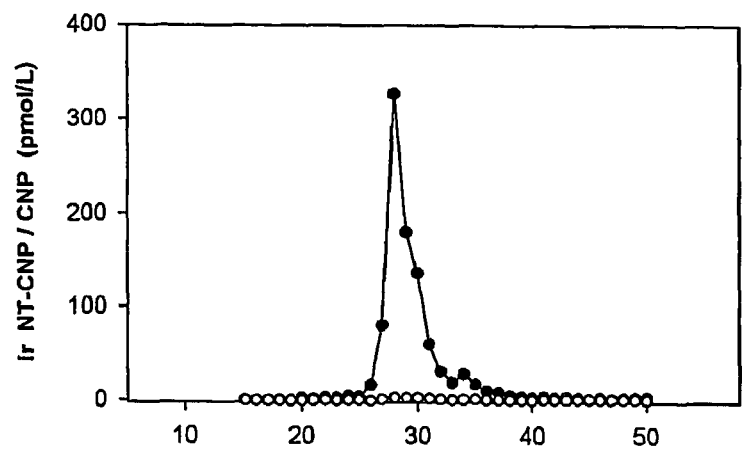
Figure 5:
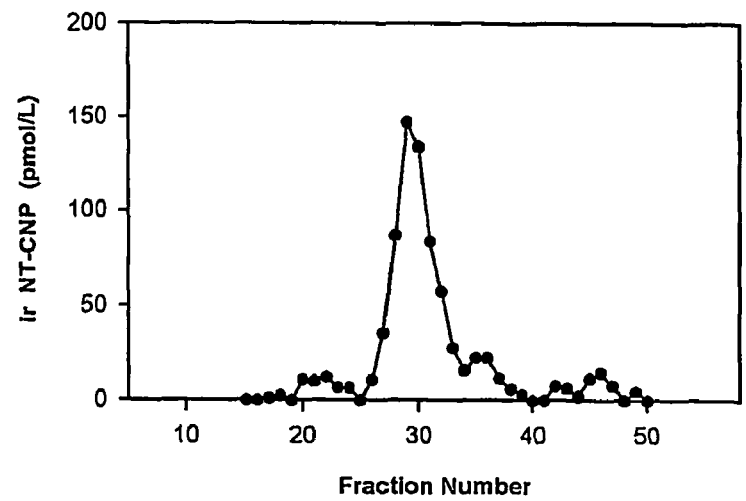
Figure 6:
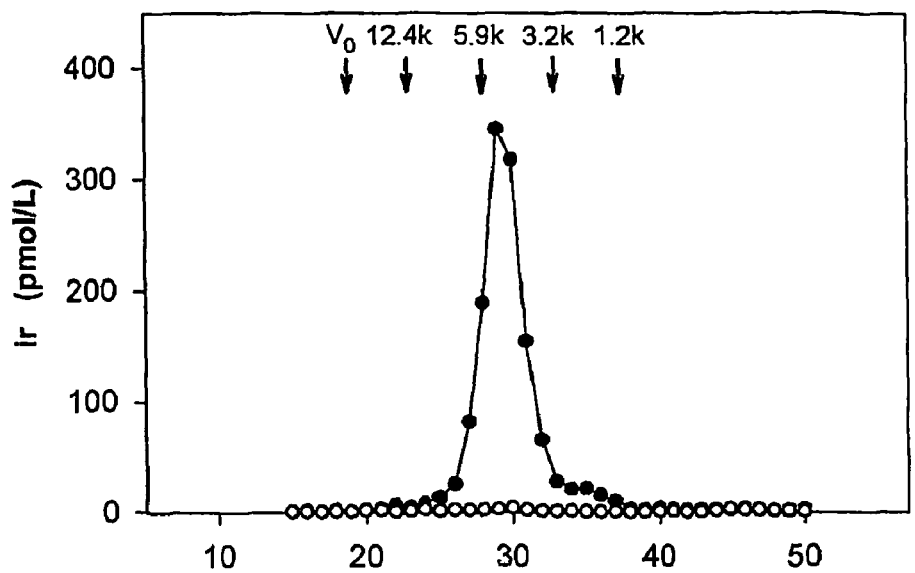
FIG. 6A and FIG. 6B show the results from size exclusion HPLC of (FIG. 6A) pooled maternal plasma and (FIG. 6B) matching pooled cord plasma. Column void volume and elution positions or molecular weight markers are shown by arrows. Immunoreactive NT-CNP (closed circles) and CNP (open circles)
Figure 6:
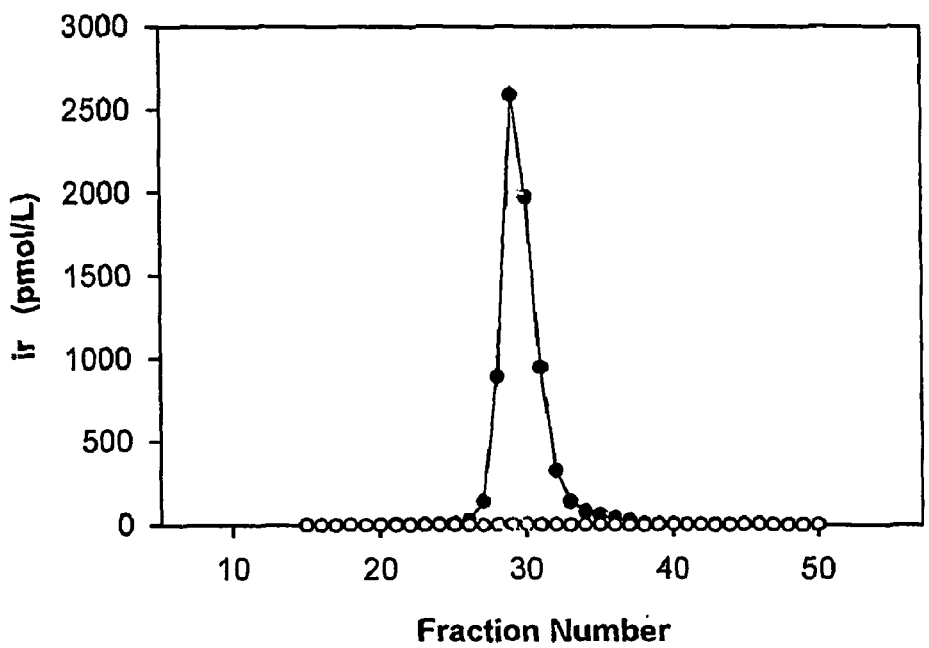

Specificity of the NT-CNP radioimmunoassay: We have established a radioimmunoassay for NT-CNP measurement using an antiserum (J39) raised in rabbits to a synthetic peptide corresponding to the first 15 amino acids of human ProCNP(1-103). A typical standard curve and parallel dilution curves of human plasma is shown in FIG. 4. This assay had an $ED_{50}$ of 110 pM and a detection limit (2 SD from zero) of 2 pM. Cross reactivities using the J39 antisera were:— hANP(99-126)<0.03%, hBNP32<0.05%, hCNP-22<0.03%, hCNP-53<0.07%. hproANP(1-30)<0.07%, hproBNP(1-21) <0.4%.

Human and ovine plasma contain NT-CNP: Plasma obtained from human umbilical cords, normal adults, children and sheep was extracted on Sep Pak columns and subjected to size exclusion HPLC (SE-HPLC) (FIG. 5A, FIG. 5B, FIG. 5C, FIG. 6A and FIG. 6B). SE-HPLC showed the major immunoreactive NT-CNP peak in all these samples had a molecular weight close to 5 kDa (fractions 29-30, FIG. 5A, FIG. 5B, FIG. 5C, FIG. 6A and FIG. 6B). No immunoreactivity to antisera raised against CNP-22 could be demonstrated in these HPLC fractions.

These results show the presence of N-terminal CNP fragment(s) in human and sheep plasma. The NT-CNP radioimmunoassay is specific for the pro-CNP(1-15) region of proCNP(1-103) and has less than 0.4% crossreactivity with CNP-22, CNP-53 and other peptides including peptide sequences from other sections of proCNP(1-103). The radioimmunoassay specificity established that the major immunoreactive NT-CNP component in human and sheep plasma contained at least some portion of the proCNP(1-15) sequence and in conjunction with size exclusion HPLC showed the major NT-CNP component had a molecular weight of 5 kDa. A minor NT-CNP component with Mr of 9 kDa was also present (1). Taken together, the data show the new NT-CNP peptides are either proCNP(1-50) (predicted Mr 5046) and proCNP(1-81) (predicted Mr 8.7 kDa) or closely similar peptides. These peptides are products expected from processing of proCNP(1-103) to proCNP(51-103) i.e. (CNP-53) and to proCNP(82-103) (CNP-22) (FIG. 1).

Figure 7:
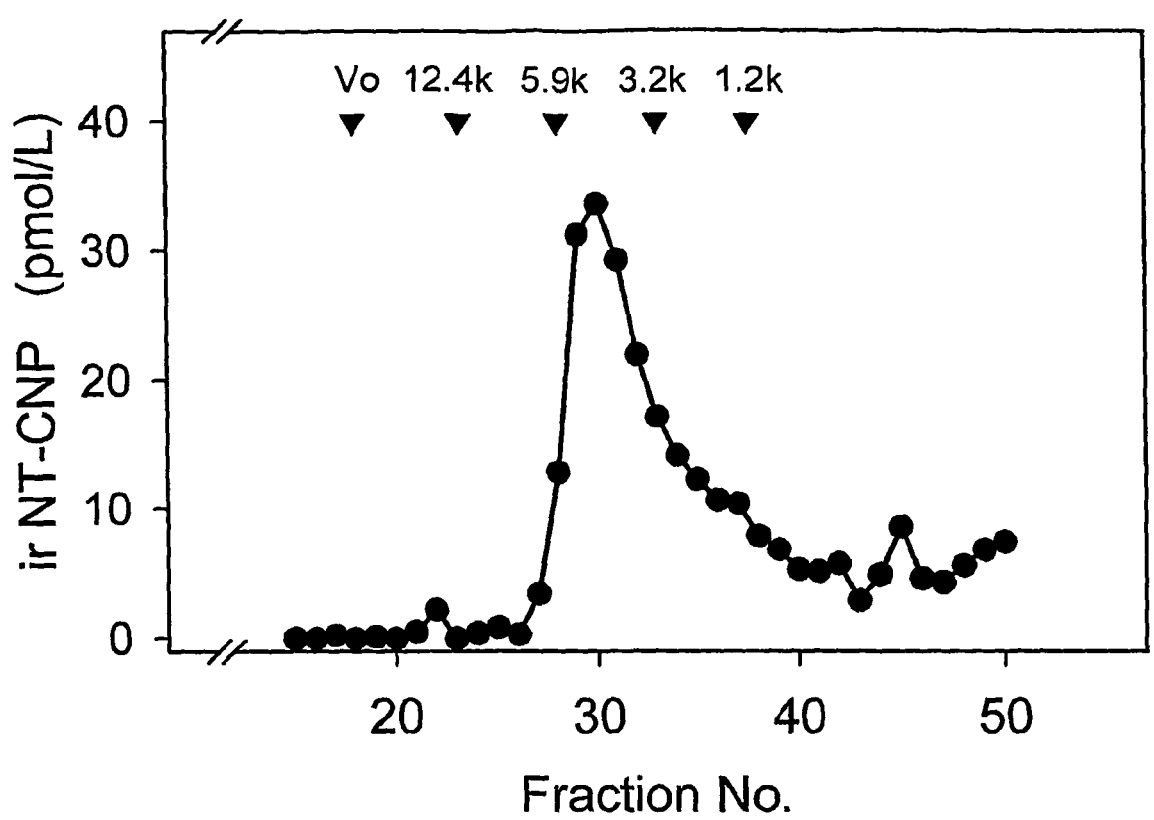
FIG. 7: shows the NT-CNP immunoreactive profile of a size exclusion HPLC of growth plate cartilage extract obtained from a fetal lamb tibia (gestation approximately 18 weeks). Column void volume ($V_o$) and elution positions of molecular markers are shown by arrows.

Ovine growth plates contain NT-CNP: Fetal tibia growth plates were boiled in water, acidified with acetic acid homogenised and centrifuged. The supernatant was extracted as for plasma and the extract submitted to size exclusion HPLC with collection of 0.5 ml fractions. Measurement of NT-CNP in the fractions showed a major peak of NT-CNP immunoreactivity eluting at a molecular weight of approximately 5000 Daltons consistent with this material being NT-CNP(1-50) or closely similar peptide FIG. 7. Quantitative analysis of growth plate extracts from four 12 week-old lambs (Table 2) revealed NT-CNP levels of 48 to 114 fmol/g—much greater than corresponding plasma NT-CNP and growth plate CNP levels.

TABLE 2

Growth Plate Tissue, Marrow and Plasma Levels of NT-CNP, CNP and Ratios in 12 week old Ewe Lambs. (Mean ± SEM, n = 4).

| Tissue | NT-CNP (fmol/g) | CNP (fmol/g) | Ratio NT-CNP/CNP |
| --- | --- | --- | --- |
| Tibia | | | |
| Proximal | 72 ± 13 | 11 ± 3 | 6.9 ± 1.2 |
| Distal | 48 ± 23 | 14 ± 7 | 3.4 ± 0.7 |
| Metatarsal | | | |
| Proximal | 114 ± 28 | 57 ± 29 | 3.2 ± 1.0 |
| Distal | 73 ± 31 | 30 ± 17 | 2.3 ± 0.6 |
| Metacarpal | | | |
| Proximal | 89 ± 10 | 33 ± 3 | 2.7 ± 0.1 |
| Distal | 84 ± 27 | 29 ± 10 | 2.7 ± 0.5 |
| Marrow (metatarsal) | 23 ± 2 | 6.6 ± 0.2 | 3.4 ± 0.2 |
| Plasma (pmol/L) | 32 ± 1 | 1.8 ± 0.1 | 22.8 ± 0.8 |

Figure 3:
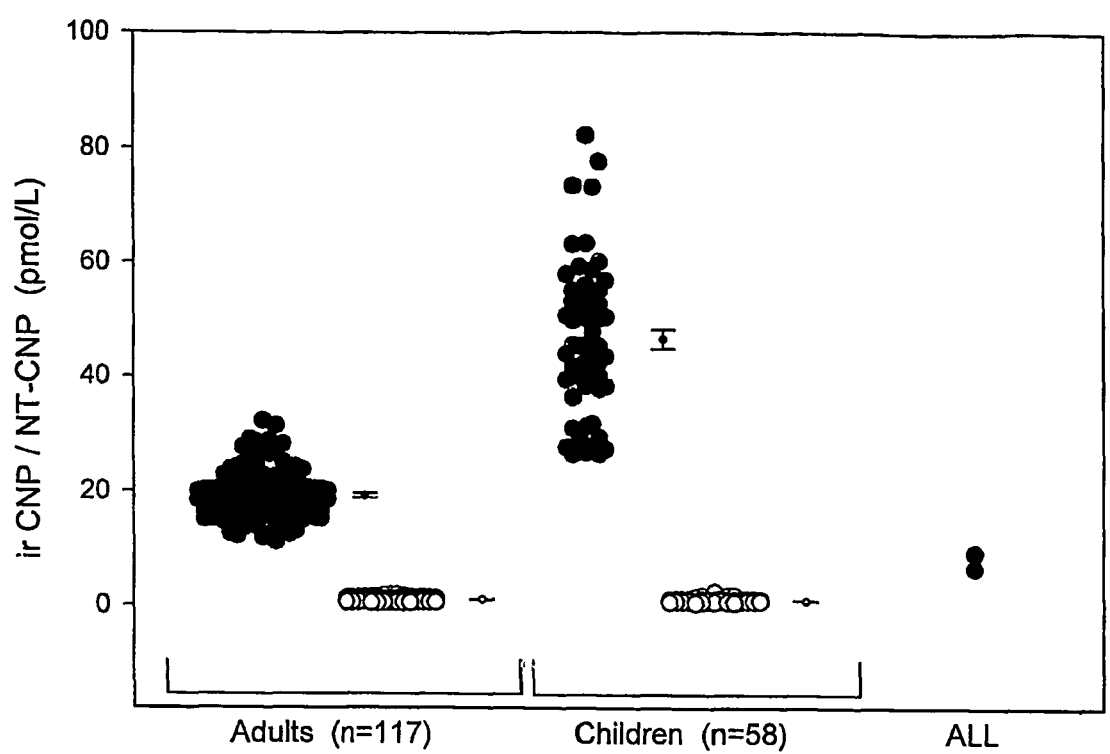
FIG. 3 Shows plasma concentrations of NT-CNP (filled circles) and CNP (open circles) in children (aged 5-18) compared to healthy adult subjects (aged 20-80 years). Mean and standard error of the mean (SEM) are also shown. Plasma NT-CNP concentrations in 2 children diagnosed with acute lymphatic leukaemia (ALL) and receiving acute chemotherapy and high dose glucocorticoids are also shown.
Figure 8:
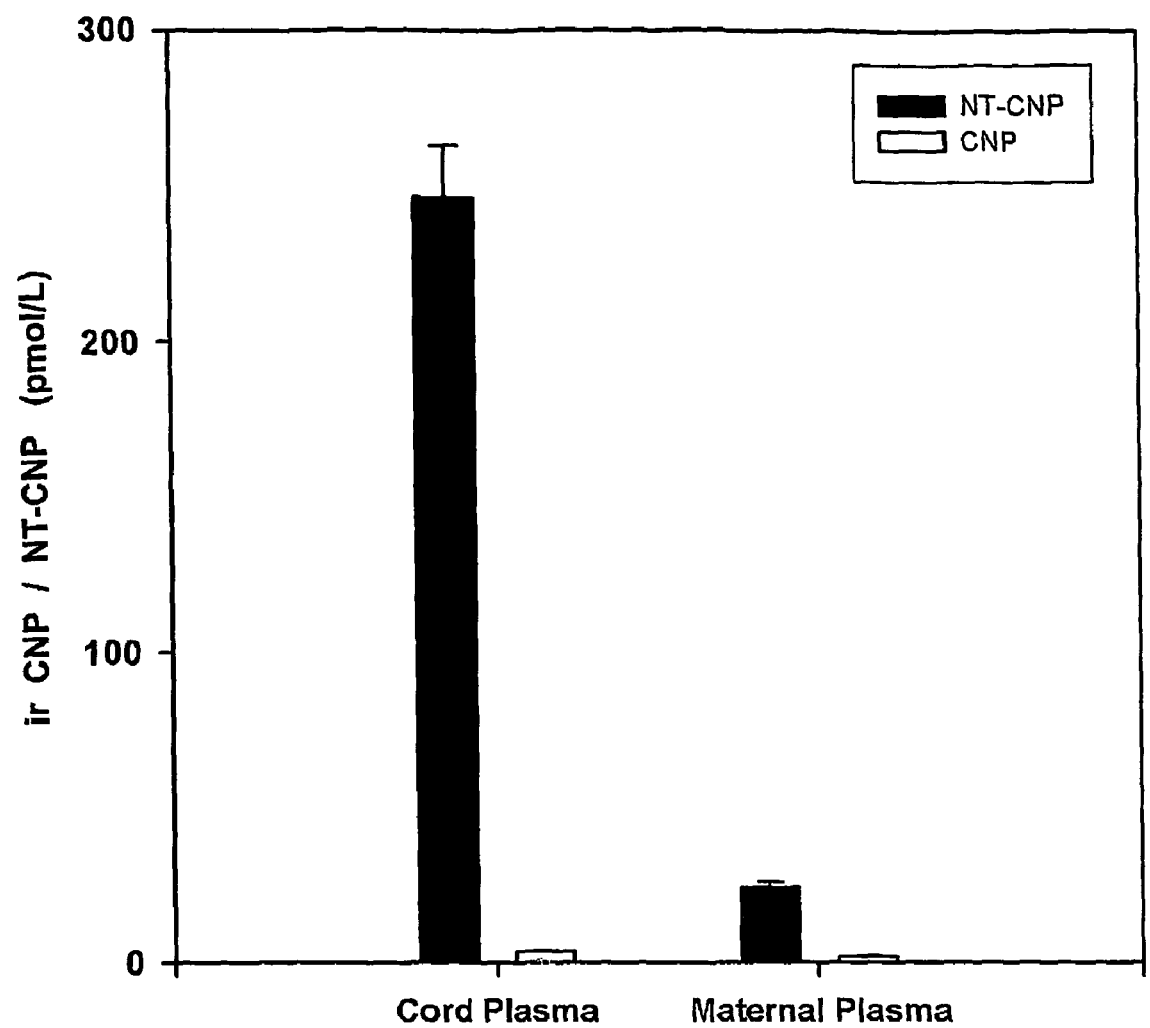
FIG. 8 is a graph showing the mean (±SEM) concentrations of NT-CNP (filled bars) and CNP (open bars) in neonatal umbilical cord plasma (left n=10) compared to maternal concentrations (right n=10) immediately after delivery.

Plasma NT-CNP levels in normal adults and children: The mean±SEM plasma levels of NT-CNP in 117 normal adults (19.2±0.4 pmol/L) are significantly higher than CNP (0.93±0.03 pmol/L; p<0.001), (FIG. 3). In children (n=58, ages 5-18 years), plasma levels of NT-CNP (46.6±1.7 pmol/L) are significantly higher than in normal adults n=117 aged 20-80 years (19.2±0.4 pmol/L), and much higher than CNP (1±0.05 pmol/L). Similarly, the massively raised NT-CNP levels found in umbilical cord blood (representing neonatal levels, mean 246±17 pmol/L, n=10) are some 60-fold higher than CNP levels measured in the same blood sample (FIG. 8).

Figure 9:
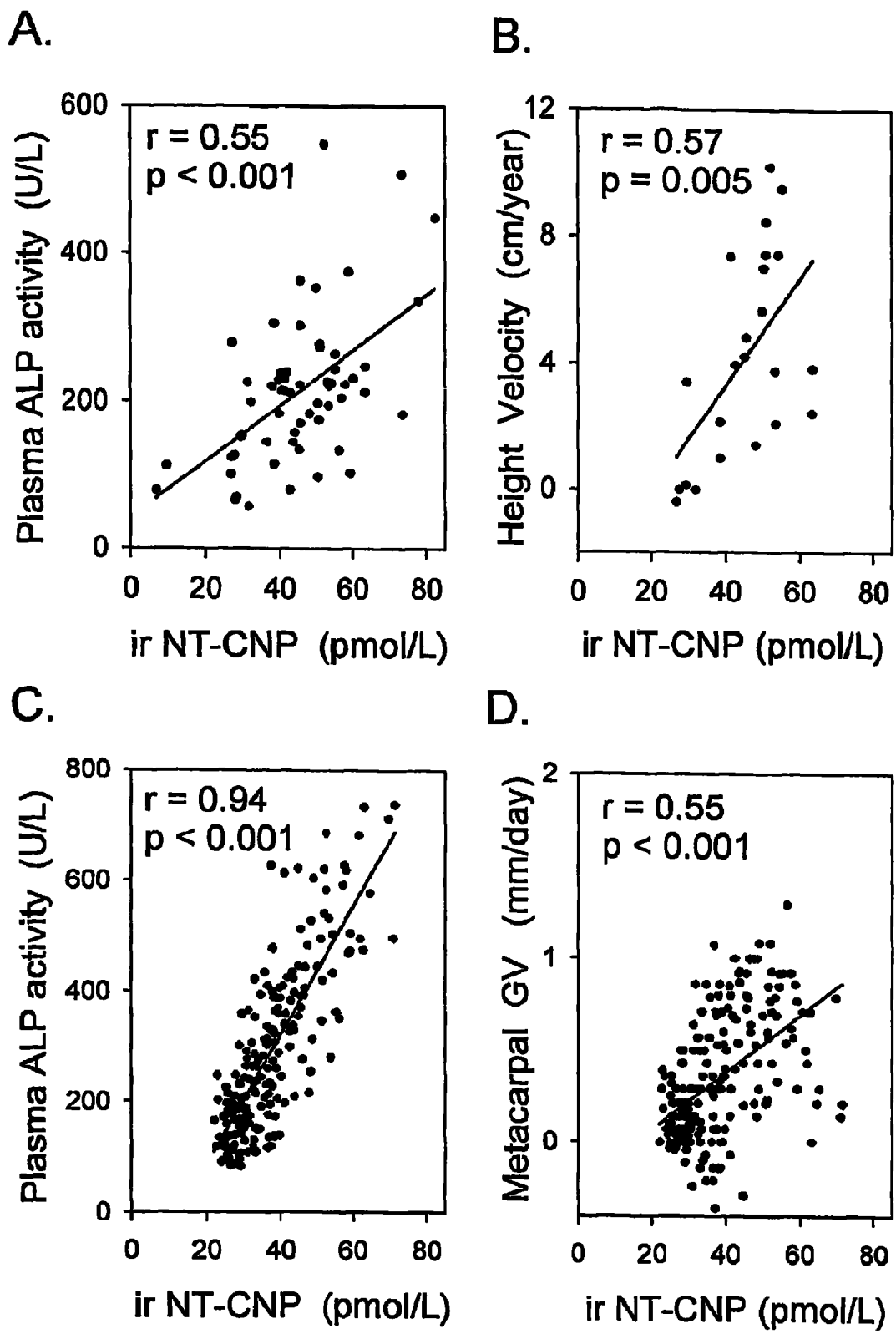
FIG. 9A, FIG. 9B, FIG. 9C and FIG. 9D: Top panels; correlations between plasma NT-CNP in children (aged 5-18 years) and (FIG. 9A) plasma alkaline phosphatase activity, (FIG. 9B) height velocity. Bottom panels; correlations between plasma NT-CNP in growing lambs and (FIG. 9C) plasma alkaline phosphatase activity, (FIG. 9D) metacarpal growth velocity.

As shown in FIG. 9A and FIG. 9B, there was a significant positive association in the 5-18 year age group between a marker of bone formation (ALP) and plasma NT-CNP (r=0.55, p<0.001), and height velocity with plasma NT-CNP (r=0.57, p=0.005).

Children receiving chemotherapy and glucocorticoids for cancer-related diseases have extremely low levels of NT-CNP (FIG. 3), indicating inhibition of cartilage proliferation and harmful effects on skeletal health and growth potential. Monitoring the level of NT-CNP in blood or other biological fluid will help in the choice of type of drug therapy and dosage.

Figure 10:
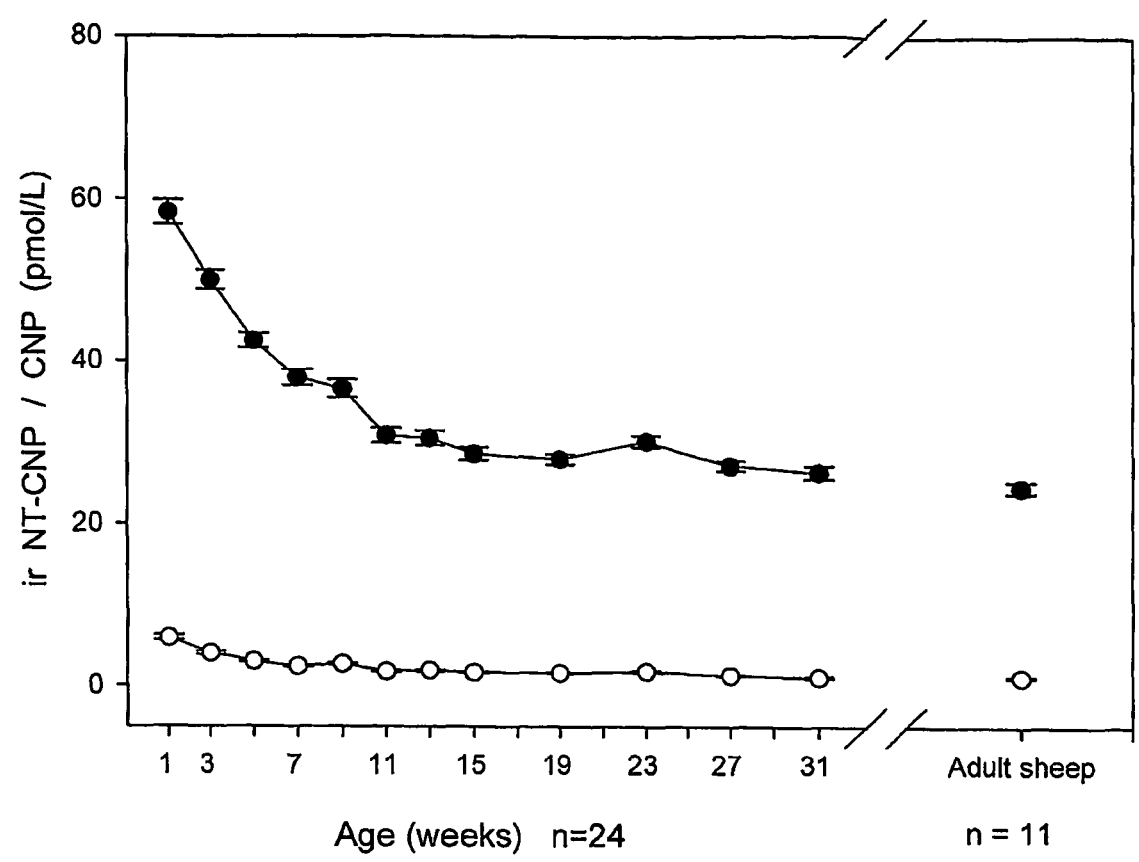
FIG. 10 is a plot of NT-CNP (filled circles) and CNP (open circles) showing the effect of aging on blood concentration in newborn lambs (n=24). Concentrations in mature adult sheep (n=11) are shown for comparison.

Plasma NT-CNP Levels in Lambs and Sheep:

Healthy young sheep (6 months of age) have levels of NT-CNP similar to adult humans (20-34 pmol/L). In 24 growing lambs plasma levels of NT-CNP were 58±2 pmol/L at 1 week of age and fell progressively over the following 26 weeks to 27±1 pmol/L (p<0.0001). Levels of CNP in these same sheep were 5.9±0.3 pmol/L (1 week) and 1.3±0.1 pmol/L at 27 weeks (FIG. 10). The progressive fall of NT-CNP in lambs is consistent with the progressive reduction in cartilage tissue in long bones as the animal matures.

As shown in FIGS. 9C and 9D, there was a highly significant positive association of NT-CNP with ALP (r=0.94, p<0.001, FIG. 9C) and with metacarpal growth velocity (r=0.55, p<0.001, FIG. 9D).

Figure 11:
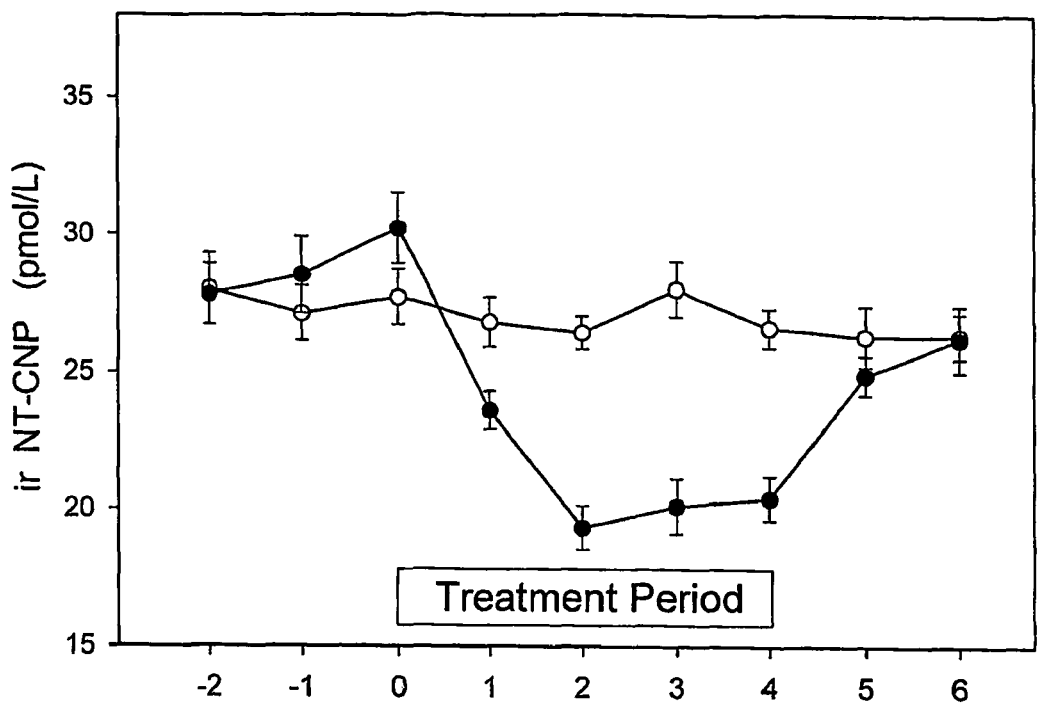
Figure 11:
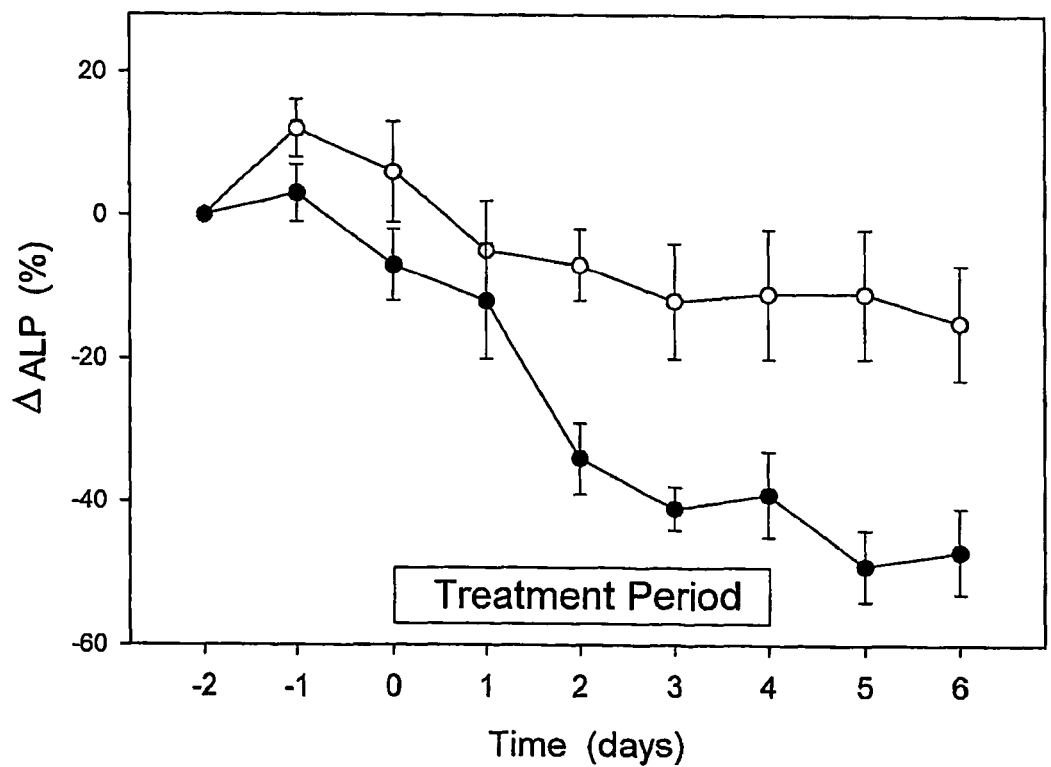
Figure 12:
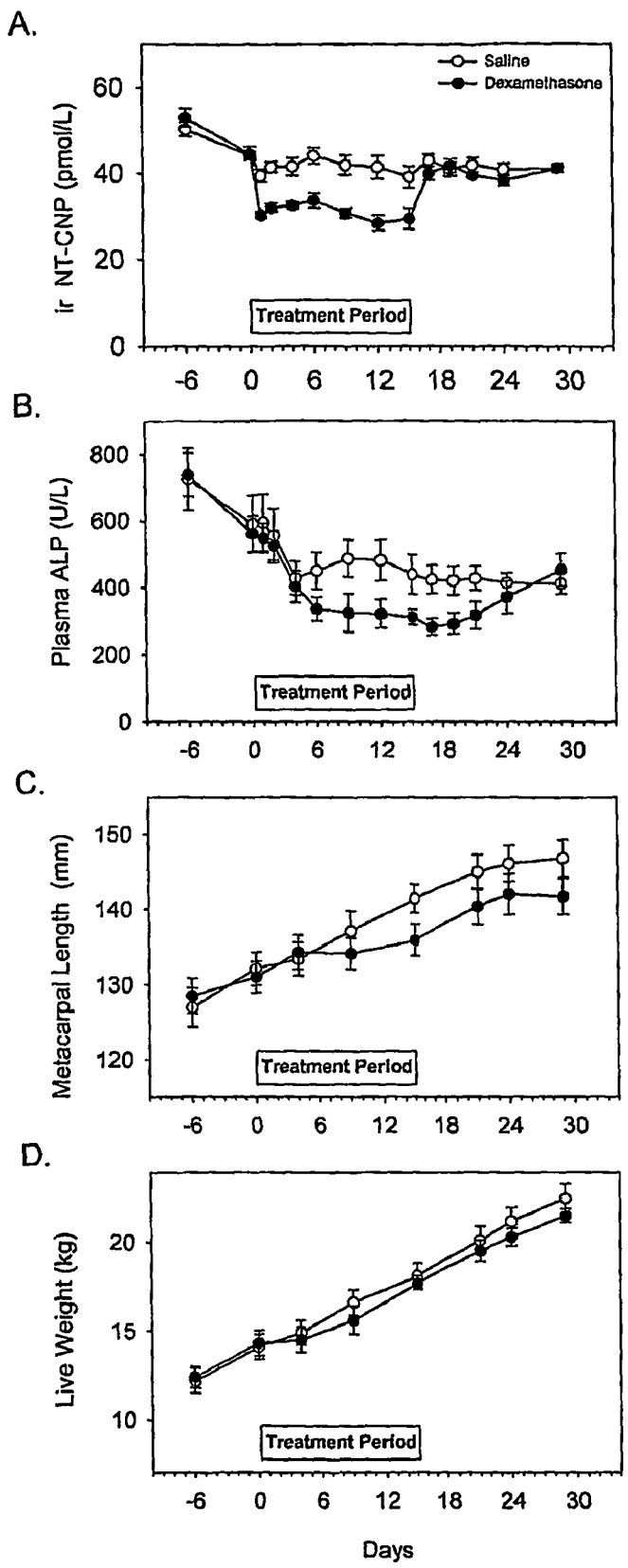

Acute administration of the glucocorticoid dexamethasone, significantly reduces the blood level of NT-CNP, as well as alkaline phosphatase (a marker of mature chondrocyte population), in growing lambs (FIG. 11A and FIG. 11B).

As shown in FIG. 11A and FIG. 11B, dexamethasone 0.25 mg/kg/day for 4 days markedly reduced plasma NT-CNP and ALP in lambs but less so in adult sheep. This differential response to dexamethasone was highly significant for both NT-CNP (F=5.4, p<0.001) and ALP (F=4.1, p=0.002). After 48 hours of dexamethasone treatment, plasma NT-CNP in lambs fell 30.8±3.5% from basal compared with 17.7±2.7% in adult sheep. Both the onset and offset of dexamethasone's action on NT-CNP preceded that of ALP (FIG. 11A and FIG. 11B). Taken together these results are consistent with the greater volume of growth plate cartilage in growing lambs, compared with adult sheep.

In order to study a possible linkage between changes in NT-CNP and growth velocity, a more prolonged study was undertaken in younger growing lambs. As shown in FIG. 12A, FIG. 12B, FIG. 12C and FIG. 12D, dexamethasone 0.25 mg/kg/day for 15 days in 4 week old lambs was associated with a highly significant fall in NT-CNP within 24 hours of starting treatment (F=7.5, p<0.001) and was sustained throughout the period of dexamethasone treatment and returned to control levels within 24 hours of cessation of treatment. Whereas plasma ALP activity also decreased during the treatment period (F=1.9, p=0.029, FIG. 12B) the onset and offset of response in ALP to dexamethasone was delayed when compared with that of NT-CNP. Dexamethasone treatment was associated with a pronounced decrease in metacarpal elongation (F=7.0, p<0.001, FIG. 12C) which abated after restoration of NT-CNP levels.

Compared with saline treated lambs, a small but significant effect of dexamethasone on body weight (F=4.4, p<0.001, FIG. 12D) was observed. However, in contrast to metacarpal elongation, differences between treatment groups at cessation of dexamethasone treatment (day 15) were not significantly different.

These results are consistent with prior art showing deleterious effects of glucocorticoids on chondrocytes and growth in children. The use of NT-CNP assays provides a totally novel and easy means of monitoring this effect.

Use of NT-CNP in the Fetus and Infants

Growth is fastest at the third trimester and in the first year after birth in humans. We have found NT-proCNP levels reflect these rapid rates and are inversely related to gestational age during the third trimester. Using NT-CNP in the fetus, umbilical cord plasma or other biological fluid in infants provides a more direct means of monitoring the infant's growth potential and response to interventions.

Use of Plasma NT-CNP as a Predictor of Growth Suppression in Subjects Receiving Glucocorticoid Therapy.

Figure 13:
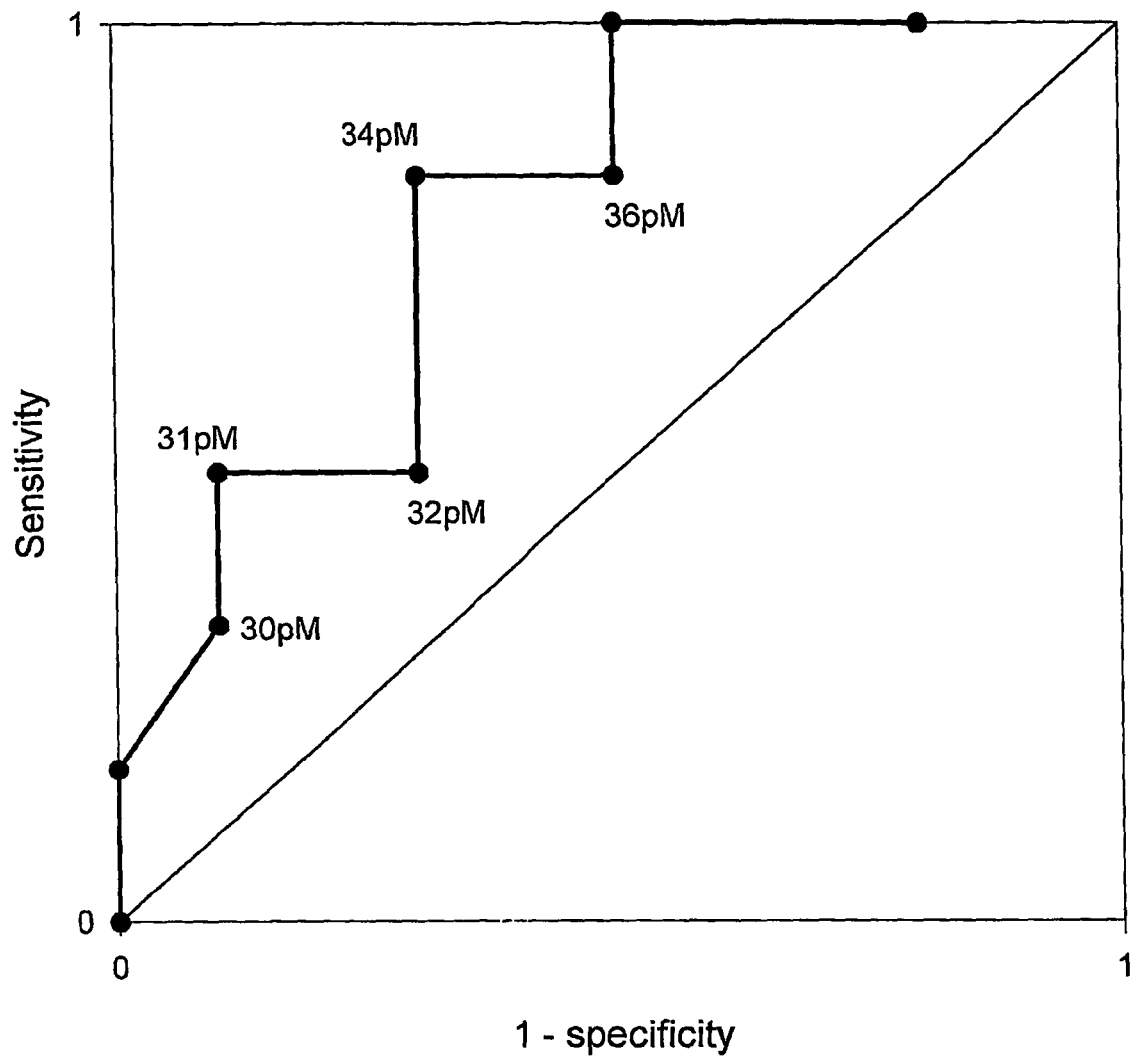

We undertook a study in normal lambs. Lambs (n=16, aged 4 weeks) either received dexamethasone (0.25 mg/kg/day) or saline injections (controls) for 15 days. The predictive effect of a plasma NT-CNP concentration (drawn 24 hours after starting treatment) on subsequent growth inhibition (defined as growth velocity less than 5% of that of control lambs) was examined by ROC curve analysis (FIG. 13). Growth inhibition was correctly predicted in 70% of all lambs exhibiting a plasma level less than 34 pmol/l. The area under the curve (AUC) was 0.85.

Therefore, early measurement of NT-CNP (within 24 hours of beginning treatment) has good predictive value (sensitivity 83%, specificity 70%) for detecting subsequent growth inhibition—and is likely to be similarly useful in children.

The assays will also have application in research studies where skeletal health and development is the subject of interest, both in humans and experimental animals or tissues.

INDUSTRIAL APPLICATION

The uses of NT-CNP and binding agents thereof in assays for the prognosis and diagnosis of disorders of growth and skeletal maturation are of industrial significance. In particular, the use of NT-CNP assays alone or in combination with measurements of other growth factors, hormones and/or plasma analytes, may be of particular significance in the healthcare industry, veterinary practice and animal husbandry.

Dr Meena P Desai, *MJAFI* 2003; 59: 278-282 states at the bottom of the left column on page 279: "Short stature is a common problem confronting the paediatrician and often the commonest cause for referral of children to endocrine services, in our experience nearly 42% of all referrals. An estimate of stunted children in developing countries gives a tentative prevalence of about 40% in children under five years, a total of about 125 million, with a general increase in prevalence with age."

Application of the present invention can detect the onset of skeletal developmental problems and thereby assist the health care professionals in treating or preventing these problems.

The antibodies described herein are applicable in immunoassay formats such as the well known Enzyme Linked Immunosorbent Assays (ELISA) or radioimmunoassays (RIA). These assays may be used to measure the concentration of NT-CNP in plasma or blood. The measured NT-CNP concentrations can then be applied to the diagnosis of conditions or diseases associated with abnormal levels of NT-CNP peptides in circulation. NT-CNP measurements may also be used to monitor conditions in subjects, to guide their treatment and to monitor their response to it.

In combination with x-rays etc, NT-CNP testing could also provide new improved methods to determine skeletal maturity and to diagnose subjects with insufficient or excessive skeletal growth rates.

In combination with other tests, NT-CNP testing (in biological fluid such as synovial fluid and/or tissues) could also provide diagnostic information in other skeletal disorders including, but not limited to, disorders of cartilage formation (e.g. tumours of the skeleton—chondromas, chondrosarcoma, osteogenic sarcoma), loss of cartilage (osteoarthritis), proliferation of cartilage (as in rheumatoid arthritis). NT-CNP testing will also be helpful in the management of fractures and in assessing rate of healing (fracture repair and bone union).

Those skilled in the art will of course appreciate that the above description is provided by way of example only and that the invention is not limited thereto.

The following references are hereby incorporated in their entirety by reference:
1. Prickett T C, Yandle T G, Nicholls M G, Espiner E A, Richards A M. Identification of amino-terminal pro-c-type natriuretic peptide in human plasma. Biochemical and Biophysical Research Communications 2001; 286(3):513-517.

2. Tanner J M, Davies P S. Clinical longitudinal standards for height and height velocity for North American children. [comment]. Journal of Pediatrics. 1985; 107(3):317-29.
3. Kohler G, Milstein C. Continuous cultures of fused cells secreting antibody of predefined specificity. Nature 1975; 256(5517):495-7.
4. Huse W D, Sastry L, Iverson S A, Kang A S, Alting-Mees M, Burton D R, Benkovic S J, Lerner R A. Generation of a large combinatorial library of the immunoglobulin repertoire in phage lambda. Science 1989; 246(4935):1275-81.
5. Harlow E, Lane D. Antibodies: a laboratory manual. Cold Spring Harbour, New York: Cold Spring Harbour Laboratory; 1988: pages 73-137.
6. Rasat R, Livesey J L, Espiner E A, Abbott G and Donald R A. IGF-1 and IGFBP-3 screening for disorders of growth hormone secretion. New Zealand Medical Journal 1996; 109(1021):156-159

What we claim is:

1. A method for assessing skeletal growth of a subject other than a patient with severe heart disease or renal failure comprising measuring N-terminal pro-C-type natriuretic peptide (NT-CNP) in a biological fluid from the subject, and comparing this measured level of NT-CNP against a mean NT-CNP level from a sex- and age-matched control population for which at least a first skeletal growth information is known, wherein a significant deviation in the measured level of NT-CNP in the subject from the mean level of NT-CNP in the control population is indicative of abnormal skeletal growth, and further wherein said measuring step comprises detecting binding between NT-CNP and an antibody that selectively binds NT-CNP.

2. The method of claim 1, wherein the biological fluid is plasma or whole blood.

3. The method of claim 1, where said subject is a pre-adult.

4. The method of claim 3, wherein said subject is a neonate and the fluid comprises cord blood.

5. The method of claim 1, wherein said subject is a pre-pubescent child or an infant.

6. The method of claim 1, wherein said subject is undergoing a treatment regimen, which may impact on skeletal growth in said subject.

7. The method of claim 1, wherein said subject is exposed to chemicals or other external factors which may impact on skeletal growth in said subject.

8. The method of claim 1, wherein said antibody is an antibody fragment that selectively binds NT-CNP.

9. The method of claim 1, wherein said antibody is a monoclonal antibody or a monoclonal antibody fragment.

10. The method of claim 1, wherein the NT-CNP to which the antibody selectively binds comprises an antigenic peptide selected from the group consisting of proCNP(1-103), proCNP(1-50), proCNP(1-81), and proCNP(51-81).

11. The method of claim 10, wherein the NT-CNP comprises proCNP(1-50).

12. The method of claim 1, wherein the antibody is immobilized to a solid phase.

13. A method for assessing skeletal growth potential of a subject other than a patient with severe heart disease or renal failure, comprising measuring N-terminal pro-C-type natriuretic peptide (NT-CNP) in a biological fluid from said subject, and comparing this measured level of NT-CNP against a mean NT-CNP level from a control sex- and age-matched population that has attained maximum skeletal growth and assessing from the NT-CNP level in the subject, whether the NT-CNP level is indicative of growth plate activity, so indicating that the subject is still growing, or whether the NT-CNP level is indicative of epiphyseal fusion so indicating that the subject has stopped growing, wherein said measuring step comprises detecting binding between NT-CNP and an antibody that selectively binds NT-CNP.

14. A method for diagnosing a skeletal disease or disorder in a subject other than a patient with severe heart disease or renal failure, comprising measuring N-terminal pro-C-type natriuretic peptide (NT-CNP) in a biological fluid from said subject, and comparing this measured level of NT-CNP against a mean NT-CNP level from a sex- and age-matched control population, wherein a significant deviation in the measured level from the mean control level is indicative of a skeletal disease or disorder, wherein said measuring step comprises detecting binding between NT-CNP and an antibody that selectively binds NT-CNP.

15. The method of claim 14, wherein where a significant deviation from the mean control level is found in the fluid, the method comprises a further step of comparing the measured NT-CNP level with one or more mean NT-CNP levels from populations having known skeletal diseases or disorders to make a more accurate diagnosis of a specific disease or disorder.

16. The method of claim 15, wherein said skeletal disease or disorder is selected from the group consisting of congenital disorders, delayed developmental disorders and advanced development syndromes.

17. The method of claim 13 or claim 14, wherein said biological fluid is plasma or whole blood.

18. The method of claim 13 or claim 14, wherein said subject is a pre-adult.

19. The method of claim 13 or claim 14, wherein said subject is a pre-pubescent child or an infant.

20. The method of claim 13 or claim 14, wherein said subject is a neonate and said biological fluid comprises cord blood.

21. The method of claim 13 or claim 14, wherein said antibody is a monoclonal antibody or a monoclonal antibody fragment thereof.

22. The method of claim 13 or claim 14, wherein the NT-CNP to which said antibody selectively binds comprises an antigenic peptide selected from the group consisting of proCNP(1-103), proCNP(1-50), proCNP(1-81), and proCNP(51-81).

23. The method of claim 22, wherein said NT-CNP comprises proCNP(1-50).

24. The method of claim 13 or claim 14, wherein the antibody is immobilized to a solid phase.

25. A method of monitoring skeletal growth in a subject other than a patient with severe heart disease or renal failure comprising:
   (a) measuring a level of N-terminal pro-C-type natriuretic peptide (NT-CNP) in a first biological fluid from said subject and measuring a level of NT-CNP in a second biological fluid, wherein said second biological fluid is taken from the same subject as said first biological fluid but at a later date; and
   (b) comparing the levels of NT-CNP in said first and said second biological fluids, wherein a significant difference in the levels of NT-CNP in said second biological fluid compared to the level of NT-CNP in said first biological fluid indicates a change in skeletal growth rate in said subject, wherein said measuring step comprises detecting binding between NT-CNP and an antibody that selectively binds NT-CNP.

26. The method of claim 25, wherein said antibody is an antibody fragment that selectively binds NT-CNP or an NT-proCNP peptide.

27. The method of claim 25, wherein said antibody is a monoclonal antibody or an antibody fragment thereof.

28. The method of claim 25, wherein said subject is undergoing a treatment regimen that may impact skeletal growth of said subject.

29. The method of claim 6 or claim 28, wherein said treatment regimen involves administration of glucocorticoids to said subject.

30. The method of claim 29, wherein said subject is undergoing treatment for asthma or other chronic allergic states.

31. A method for assessing skeletal growth of a pre-adult subject other than a patient with severe heart disease or renal failure, comprising measuring N-terminal pro-C-type natriuretic peptide (NT-CNP) in a biological fluid from the subject, and comparing this measured level of NT-CNP against a mean NT-CNP level from a sex- and age-matched control population for which at least a first skeletal growth information is known, wherein a significant deviation in the measured level of NT-CNP in the subject from the mean level of NT-CNP in the control population is indicative of abnormal skeletal growth, wherein said measuring step comprises detecting binding between NT-CNP and an antibody, or an antibody fragment thereof, that selectively binds NT-CNP or an NT-proCNP peptide.

32. The method of claim 31, wherein said NT-proCNP peptide comprises an antigenic peptide selected from the group consisting of proCNP(1-103), proCNP(1-50), proCNP(1-81), and proCNP(51-81).

33. A method for assessing skeletal growth of a subject other than a patient with severe heart disease or renal failure suspected of having a skeletal disease or disorder, comprising measuring N-terminal pro-C-type natriuretic peptide (NT-CNP) in a biological fluid from the subject, and comparing this measured level of NT-CNP against a mean NT-CNP level from a sex- and age-matched control population for which at least a first skeletal growth information is known, wherein a significant deviation in the measured level of NT-CNP in the subject from the mean level of NT-CNP in the control population is indicative of abnormal skeletal growth in said subject, wherein said measuring step comprises detecting binding between NT-CNP and an antibody, or an antibody fragment thereof, that selectively binds NT-CNP or an NT-proCNP peptide.

34. The method of claim 33, wherein said NT-proCNP peptide comprises an antigenic peptide selected from the group consisting of proCNP(1-103), proCNP(1-50), proCNP(1-81), and proCNP(51-81).

* * * * *